US011021689B2

(12) United States Patent
Brument

(10) Patent No.: US 11,021,689 B2
(45) **Date of Patent: *Jun. 1, 2021**

(54) RECOMBINANT ADENO-ASSOCIATED VIRUS PARTICLE PURIFICATION COMPRISING AN AFFINITY PURIFICATION STEP

(71) Applicants: INSTITUT NATIONAL DE LA SANTE ET DE LA RECHERCHE MEDICALE (INSERM), Paris (FR); UNIVERSITE DE NANTES, Nantes (FR); CHU NANTES, Nantes (FR); ASSOCIATION FRANCAISE CONTRE LES MYOPATHIES, Paris (FR)

(72) Inventor: Nicole Brument, Nantes (FR)

(73) Assignees: INSTITUT NATIONAL DE LA SANTE ET DE LA RECHERCHE MEDICALE (INSERM), Paris (FR); UNIVERSITE DE NANTER, Nantes (FR); CHU NANTES, Nantes (FR); ASSOCIATION FRANCAISE CONTRE LES MYOPATHIES, Paris (FR)

( * ) Notice: Subject to any disclaimer, the term of this patent is extended or adjusted under 35 U.S.C. 154(b) by 435 days.

This patent is subject to a terminal disclaimer.

(21) Appl. No.: 15/549,186

(22) PCT Filed: Feb. 9, 2016

(86) PCT No.: PCT/EP2016/052740

§ 371 (c)(1),
(2) Date: Aug. 7, 2017

(87) PCT Pub. No.: WO2016/128408

PCT Pub. Date: Aug. 18, 2016

(65) Prior Publication Data

US 2019/0382733 A1 Dec. 19, 2019

(30) Foreign Application Priority Data

Feb. 9, 2015 (EP) .................................... 15305188

(51) Int. Cl.

| | |
|---|---|
| ***C12N 7/00*** | (2006.01) |
| ***A61K 48/00*** | (2006.01) |
| ***C12N 9/16*** | (2006.01) |
| ***C12N 9/18*** | (2006.01) |
| ***C12N 15/86*** | (2006.01) |
| *A61P 9/10* | (2006.01) |
| *A61P 27/02* | (2006.01) |

(52) U.S. Cl.

CPC ............ *C12N 7/00* (2013.01); *A61K 48/0091* (2013.01); *C12N 9/16* (2013.01); *C12N 9/18* (2013.01); *C12N 15/86* (2013.01); *C12Y 301/01064* (2013.01); *C12Y 301/04035* (2013.01); *A61P 9/10* (2018.01); *A61P 27/02* (2018.01); *C12N 2750/14143* (2013.01); *C12N 2750/14151* (2013.01)

(58) Field of Classification Search

CPC .............. B01D 15/363; B01D 2257/91; C12N 2750/14151; C12N 7/00; C12N 7/02

USPC ................................. 435/320.1, 235.1, 69.1

See application file for complete search history.

(56) References Cited

U.S. PATENT DOCUMENTS

| | | | |
|---|---|---|---|
| 5,139,941 | A | 8/1992 | Muzyczka et al. |
| 5,713,414 | A | 2/1998 | Ko |

(Continued)

FOREIGN PATENT DOCUMENTS

| | | |
|---|---|---|
| WO | 1992001070 | 1/1992 |
| WO | 1993003769 | 3/1993 |

(Continued)

OTHER PUBLICATIONS

Oksanen et al., “Monolithic ion exchange chromatographic methods for virus purification,” Virology 434: 271-277 (Year: 2012).*

(Continued)

*Primary Examiner* — Janet L Epps-Smith

(74) *Attorney, Agent, or Firm* — W&C IP

(57) ABSTRACT

The invention describes a method for obtaining purified recombinant Adeno-Associated Virus particles (rAAV), comprising the steps of: a) performing a depth filtration of a starting material previously obtained from cells producing rAAV particles, the said starting material being selected in a group comprising a cell lysate and a culture supernatant, whereby a rAAV-containing clarified composition is provided; b) submitting the rAAV-containing clarified composition to an affinity purification step, whereby a first rAAV enriched composition is provided; c) submitting the first rAAV enriched composition at least once to: c1) a step of anion-exchange chromatography on a chromatographic support wherein elution is performed by using a salt gradient, preferably a linear salt gradient, and wherein the rAAV-containing fraction is collected, whereby a second rAAV enriched composition is provided; or c2) a step of density gradient centrifugation, wherein the rAAV-containing fraction is collected, whereby a second rAAV enriched composition is provided; d) submitting the second rAAV enriched composition to a step of tangential flow filtration, whereby purified recombinant Adeno-Associated Virus particles (rAAV) are provided.

12 Claims, 5 Drawing Sheets

Specification includes a Sequence Listing.

(56) References Cited

U.S. PATENT DOCUMENTS

| | | | | |
|---|---|---|---|---|
| 6,376,237 | B1 | 4/2002 | Colosi | |
| 2004/0106184 | A1* | 6/2004 | Senesac | C12N 7/00 435/239 |

FOREIGN PATENT DOCUMENTS

| | | | | |
|---|---|---|---|---|
| WO | 2002012455 | A1 | 2/2002 | |
| WO | 2003097797 | | 12/2003 | |
| WO | 2010/148143 | A1 | 12/2010 | |
| WO | WO-2010148143 | A1 * | 12/2010 | C12N 7/00 |
| WO | 2011/094198 | A1 | 8/2011 | |
| WO | 2013036118 | A1 | 3/2013 | |

OTHER PUBLICATIONS

Allocca et al., Investigative Opthamology & Visual Science vol. 52, No. 8: 5713-5719 (Year: 2011).*

Brument et al. ("A Versatile and Scalable Two-Step Ion-Exchange Chromatography Process for the Purification of Recombinant Adeno-associated Virus Serotypes-2 and -5," Molecular Therapy, vol. 6, No. 5: 678-686 (2002)) (Year: 2002).*

Hordeauxetal. Gene Therapy (2015) 22, 316-324. (Year: 2015).*

Lemeuretal. (Gene Therapy, vol. 14, 292-303, 2007) (Year: 2007).*

Wang et al. Chapter 16 or Richard O. Snyder and Philippe Moullier (eds.), Adeno-Associated Virus: Methods and Protocols, Methods in Molecular Biology, vol. 807, DOI 10.1007/978-1-61779-370-7_16, © Springer Science+Business Media, LLC 2011. (Year: 2011).*

Kaludovetal. Human Gene Therapy 13:1235-1243 (Jul. 1, 2002) (Year: 2002).*

Ayuso et al., "Manufacturing and characterization of a recombinant adeno-associated virus type 8 reference standard material". Hum Gene Ther. Nov. 2014;25(11):977-87.

Berns & Bohensky, 1987. "Adeno-associated viruses: an update". In Maramorosch, Murphy, & Shatkin (Eds.), Advances in Virus Research (vol. 32, pp. 243-307). New York, NY: Academic Press, Inc.

Carter, "Adeno-associated virus vectors". Curr Opin Biotechnol. Oct. 1992;3(5):533-9.

Chu et al., "SV40 DNA transfection of cells in suspension: analysis of efficiency of transcription and translation of T-antigen". Gene. Mar. 1981;13(2):197-202.

Cole et al., "Human monoclonal antibodies". Mol Cell Biochem. Jun. 1984;62(2):109-20.

Cote et al., "Generation of human monoclonal antibodies reactive with cellular antigens". Proc Natl Acad Sci U S A. Apr. 1983;80(7):2026-30.

Davis et al., 1986. "Basic methods in molecular biology", (1st ed.). New York, NY: Elsevier.

Braham et al., "A new technique for the assay of infectivity of human adenovirus 5 DNA". Virology. Apr. 1973;52(2):456-67.

Heukeshoven & Demick, "Characterization of a solvent system for separation of water-insoluble poliovirus proteins by reversed-phase high-performance liquid chromatography". J Chromatogr. Jun. 19, 1985;326:91-101.

Köhler & Milstein, "Continuous cultures of fused cells secreting antibody of predefined specificity". Nature. Aug. 7, 1975;256(5517):495-7.

Kotin, "Prospects for the use of adeno-associated virus as a vector for human gene therapy". Hum Gene Ther. Jul. 1994;5(7):793-801.

Kozbor et al., "Specific immunoglobulin production and enhanced tumorigenicity following ascites growth of human hybridomas". J Immunol Methods. Jul. 16, 1985;81(1):31-42.

Le Meur et al., "Restoration of vision in RPE65-deficient Briard dogs using an AAV serotype 4 vector that specifically targets the retinal pigmented epithelium". Gene Ther. Feb. 2007;14(4):292-303.

Lebkowski et al., "Adeno-associated virus: a vector system for efficient introduction and integration of DNA into a variety of mammalian cell types". Mol Cell Biol. Oct. 1988;8(10):3988-96.

McCarty et al., "Sequences required for coordinate induction of adeno-associated virus p19 and p40 promoters by Rep protein". J Virol. Jun. 1991;65(6):2936-45.

Moser & Hage, "Immunoaffinity chromatography: an introduction to applications and recent developments". Bioanalysis. Apr. 2010;2(4):769-90.

Muzyczka, "Use of adeno-associated virus as a general transduction vector for mammalian cells". Curr Top Microbiol Immunol. 1992;158:97-129.

Petit et al., "Restoration of vision in the pde6β-deficient dog, a large animal model of rod-cone dystrophy". Mol Ther. Nov. 2012;20(11):2019-30.

Pulicherla & Asokan, "Peptide affinity reagents for AAV capsid recognition and purification". Gene Ther. Oct. 2011;18(10):1020-4.

Salvetti et al., "Factors influencing recombinant adeno-associated virus production". Hum Gene Ther. Mar. 20, 1998;9(5):695-706.

Samulski et al., "Helper-free stocks of recombinant adeno-associated viruses: normal integration does not require viral jene expression". J Virol. Sep. 1989;63(9):3822-8.

Zolotukhin et al., "Recombinant adeno-associated virus purification using novel methods improves infectious titer and yield". Gene Ther. Jun. 1999;6(6):973-85.

* cited by examiner

SEQUENCE LISTING

```
<160> NUMBER OF SEQ ID NOS: 15

<210> SEQ ID NO 1
<211> LENGTH: 3505
<212> TYPE: DNA
<213> ORGANISM: Artificial Sequence
<220> FEATURE:
<223> OTHER INFORMATION: Synthetic Expression cassette encoding human
      PDE6beta

<400> SEQUENCE: 1

ctgcgcgctc gctcgctcac tgaggccgcc cgggcaaagc ccgggcgtcg ggcgaccttt     60

ggccgggcgg cctcagtgag cgagcgagcg cgcagagagg gagtggccaa ctccatcact    120

aggggttcct tgtagttaat gattaacccg ccatgctact tatctacgac attgattatt    180

gactagtccg gatccaagct cagatctcga gttgggcccc agaagcctgg tggttgtttg    240

tccttctcag gggaaaagtg aggcggcccc ttggaggaag gggccgggca gaatgatcta    300

atcggattcc aagcagctca ggggattgtc tttttctagc accttcttgc cactcctaag    360

cgtcctccgt gaccccggct gggatttagc ctggtgctgt gtcagccccg ggtcgacaag    420

cttggatcca tgagcctcag tgaggagcag gcccggagct ttctggacca gaaccccgat    480

tttgcccgcc agtactttgg gaagaaactg agccctgaga atgtggccgc ggcctgcgag    540

gacgggtgcc cgccggactg cgacagcctc cgggacctct gccaggtgga ggagagcacg    600

gcgctgctgg agctggtgca ggatatgcag gagagcatca acatggagcg cgtggtcttc    660

aaggtcctgc ggcgcctctg caccctcctg caggccgacc gctgcagcct cttcatgtac    720

cgccagcgca acggcgtggc cgagctggcc accaggcttt tcagcgtgca gccggacagc    780

gtcctggagg actgcctggt gccccccgac tccgagatcg tcttcccact ggacatcggg    840

gtcgtgggcc acgtggctca gaccaaaaag atggtgaacg tcgaggacgt ggccgagtgc    900

cctcacttca gctcatttgc tgacgagctc actgactaca agacaaagaa tatgctggcc    960

acacccatca tgaatggcaa agacgtcgtg gcggtgatca tggcagtgaa caagctcaac   1020

ggcccattct tcaccagcga agacgaagat gtgttcttga agtacctgaa ttttgccacg   1080

ttgtacctga agatctatca cctgagctac ctccacaact gcgagacgcg ccgcggccag   1140

gtgctgctgt ggtcggccaa caaggtgttt gaggagctga cggacatcga gaggcagttc   1200

cacaaggcct tctacacggt gcgggcctac ctcaactgcg agcggtactc cgtgggcctc   1260

ctggacatga ccaaggagaa ggaatttttt gacgtgtggt ctgtgctgat gggagagtcc   1320

cagccgtact cgggcccacg cacgcctgat ggccgggaaa ttgtcttcta caaagtgatc   1380

gactacatcc tccacggcaa ggaggagatc aaggtcattc ccacaccctc agccgatcac   1440

tgggccctgg ccagcggcct tccaagctac gtggcagaaa gcggctttat ttgtaacatc   1500

atgaatgctt ccgctgacga aatgttcaaa tttcaggaag gggccctgga cgactccggg   1560
```

```
tggctcatca agaatgtgct gtccatgccc atcgtcaaca agaaggagga gattgtggga   1620

gtcgccacat tttacaacag gaaagacggg aagccctttg acgaacagga cgaggttctc   1680

atggagtccc tgacacagtt cctgggctgg tcagtgatga acaccgacac ctacgacaag   1740

atgaacaagc tggagaaccg caaggacatc gcacaggaca tggtccttta ccacgtgaag   1800

tgcgacaggg acgagatcca gctcatcctg ccaaccagag cgcgcctggg gaaggagcct   1860

gctgactgcg atgaggacga gctgggcgaa atcctgaagg aggagctgcc agggcccacc   1920

acatttgaca tctacgaatt ccacttctct gacctggagt gcaccgaact ggacctggtc   1980

aaatgtggca tccagatgta ctacgagctg ggcgtggtcc gaaagttcca gatcccccag   2040

gaggtcctgg tgcggttcct gttctccatc agcaaagggt accggagaat cacctaccac   2100

aactggcgcc acggcttcaa cgtggcccag acgatgttca cgctgctcat gaccggcaaa   2160

ctgaagagct actacacgga cctggaggcc ttcgccatgg tgacagccgg cctgtgccat   2220

gacatcgacc accgcggcac caacaacctg taccagatga agtcccagaa ccccttggct   2280

aagctccacg gctcctcgat tttggagcgg caccacctgg agtttgggaa gttcctgctc   2340

tcggaggaga ccctgaacat ctaccagaac ctgaaccggc ggcagcacga gcacgtgatc   2400

cacctgatgg acatcgccat catcgccacg gacctggccc tgtacttcaa gaagagagcg   2460

atgtttcaga agatcgtgga tgagtccaag aactaccagg acaagaagag ctgggtggag   2520

tacctgtccc tggagacgac ccggaaggag atcgtcatgg ccatgatgat gacagcctgc   2580

gacctgtctg ccatcaccaa gccctgggaa gtccagagca aggtcgcact tctcgtggct   2640

gctgagttct gggagcaagg tgacttggaa aggacagtct tggatcagca gcccattcct   2700

atgatggacc ggaacaaggc ggccgagctc cccaagctgc aagtgggctt catcgacttc   2760

gtgtgcacat tcgtgtacaa ggagttctct cgtttccacg aagagatcct gcccatgttc   2820

gaccgactgc agaacaatag gaaagagtgg aaggcgctgg ctgatgagta tgaggccaaa   2880

gtgaaggctc tggaggagaa ggaggaggag gagagggtgg cagccaagaa agtaggcaca   2940

gaaatttgca atggcggccc agcacccaag tcttcaacct gctgtatcct gtgagatatc   3000

agcgctttaa atttgcgcat gctagctata gttctagagg gccctattct atagtgtcac   3060

ctaaatgcta gagctcgctg atcagcctcg actgtgcctt ctagttgcca gccatctgtt   3120

gtttgcccct cccccgtgcc ttccttgacc ctggaaggtg ccactcccac tgtcctttcc   3180

taataaaatg aggaaattgc atcgcattgt ctgagtaggt gtcattctat tctggggggt   3240

ggggtggggc aggacagcaa gggggaggat tgggaagaca atagcaggca tgctggggat   3300

gcggtgggct ctatggcttc tgaggcggaa agaaccaggt agataagtag catggcgggt   3360

taatcattaa ctacaaggaa cccctagtga tggagttggc cactccctct ctgcgcgctc   3420

gctcgctcac tgaggccggg cgaccaaagg tcgcccgacg cccgggcttt gcccgggcgg   3480

cctcagtgag cgagcgagcg cgcag                                         3505
```

<210> SEQ ID NO 2
<211> LENGTH: 2565
<212> TYPE: DNA
<213> ORGANISM: Homo sapiens

<400> SEQUENCE: 2

```
atgagcctca gtgaggagca ggcccggagc tttctggacc agaaccccga ttttgcccgc     60

cagtactttg ggaagaaact gagccctgag aatgtggccg cggcctgcga ggacgggtgc    120
```

-continued

```
ccgccggact gcgacagcct ccgggacctc tgccaggtgg aggagagcac ggcgctgctg    180
gagctggtgc aggatatgca ggagagcatc aacatggagc gcgtggtctt caaggtcctg    240
cggcgcctct gcaccctcct gcaggccgac cgctgcagcc tcttcatgta ccgccagcgc    300
aacggcgtgg ccgagctggc caccaggctt ttcagcgtgc agccggacag cgtcctggag    360
gactgcctgg tgcccccga ctccgagatc gtcttcccac tggacatcgg ggtcgtgggc    420
cacgtggctc agaccaaaaa gatggtgaac gtcgaggacg tggccgagtg ccctcacttc    480
agctcatttg ctgacgagct cactgactac aagacaaaga atatgctggc cacacccatc    540
atgaatggca aagacgtcgt ggcggtgatc atggcagtga acaagctcaa cggcccattc    600
ttcaccagcg aagacgaaga tgtgttcttg aagtacctga attttgccac gttgtacctg    660
aagatctatc acctgagcta cctccacaac tgcgagacgc gccgcggcca ggtgctgctg    720
tggtcggcca acaaggtgtt tgaggagctg acggacatcg agaggcagtt ccacaaggcc    780
ttctacacgg tgcgggccta cctcaactgc gagcggtact ccgtgggcct cctggacatg    840
accaaggaga aggaattttt tgacgtgtgg tctgtgctga tgggagagtc ccagccgtac    900
tcgggcccac gcacgcctga tggccgggaa attgtcttct acaaagtgat cgactacatc    960
ctccacggca aggaggagat caaggtcatt cccacaccct cagccgatca ctgggccctg   1020
gccagcggcc ttccaagcta cgtggcagaa agcggcttta tttgtaacat catgaatgct   1080
tccgctgacg aaatgttcaa atttcaggaa ggggccctgg acgactccgg gtggctcatc   1140
aagaatgtgc tgtccatgcc catcgtcaac aagaaggagg agattgtggg agtcgccaca   1200
ttttacaaca ggaaagacgg gaagcccttt gacgaacagg acgaggttct catggagtcc   1260
ctgacacagt tcctgggctg gtcagtgatg aacaccgaca cctacgacaa gatgaacaag   1320
ctggagaacc gcaaggacat cgcacaggac atggtccttt accacgtgaa gtgcgacagg   1380
gacgagatcc agctcatcct gccaaccaga gcgcgcctgg ggaaggagcc tgctgactgc   1440
gatgaggacg agctgggcga aatcctgaag gaggagctgc cagggcccac cacatttgac   1500
atctacgaat tccacttctc tgacctggag tgcaccgaac tggacctggt caaatgtggc   1560
atccagatgt actacgagct gggcgtggtc cgaaagttcc agatccccca ggaggtcctg   1620
gtgcggttcc tgttctccat cagcaaaggg taccggagaa tcacctacca caactggcgc   1680
cacggcttca acgtggccca gacgatgttc acgctgctca tgaccggcaa actgaagagc   1740
tactacacgg acctggaggc cttcgccatg gtgacagccg gcctgtgcca tgacatcgac   1800
caccgcggca ccaacaacct gtaccagatg aagtcccaga acccccttggc taagctccac   1860
ggctcctcga ttttggagcg gcaccacctg gagtttggga agttcctgct ctcggaggag   1920
accctgaaca tctaccagaa cctgaaccgg cggcagcacg agcacgtgat ccacctgatg   1980
gacatcgcca tcatcgccac ggacctggcc ctgtacttca agaagagagc gatgtttcag   2040
aagatcgtgg atgagtccaa gaactaccag gacaagaaga gctgggtgga gtacctgtcc   2100
ctggagacga cccggaagga gatcgtcatg gccatgatga tgacagcctg cgacctgtct   2160
gccatcacca agccctggga agtccagagc aaggtcgcac ttctcgtggc tgctgagttc   2220
tgggagcaag gtgacttgga aaggacagtc ttggatcagc agcccattcc tatgatggac   2280
cggaacaagg cggccgagct ccccaagctg caagtgggct tcatcgactt cgtgtgcaca   2340
ttcgtgtaca aggagttctc tcgtttccac gaagagatcc tgcccatgtt cgaccgactg   2400
cagaacaata ggaaagagtg gaaggcgctg gctgatgagt atgaggccaa agtgaaggct   2460
ctggaggaga aggaggagga ggagagggtg gcagccaaga aagtaggcac agaaatttgc   2520
```

```
aatggcggcc cagcacccaa gtcttcaacc tgctgtatcc tgtga                2565


<210> SEQ ID NO 3
<211> LENGTH: 130
<212> TYPE: DNA
<213> ORGANISM: Artificial Sequence
<220> FEATURE:
<223> OTHER INFORMATION: 5' ITR derived from AAV-2

<400> SEQUENCE: 3

ctgcgcgctc gctcgctcac tgaggccgcc cgggcaaagc ccgggcgtcg ggcgaccttt     60

ggccgggcgg cctcagtgag cgagcgagcg cgcagagagg gagtggccaa ctccatcact    120

aggggttcct                                                           130


<210> SEQ ID NO 4
<211> LENGTH: 130
<212> TYPE: DNA
<213> ORGANISM: Artificial Sequence
<220> FEATURE:
<223> OTHER INFORMATION: 3' ITR derived from AAV-2

<400> SEQUENCE: 4

aggaacccct agtgatggag ttggccactc cctctctgcg cgctcgctcg ctcactgagg     60

ccgggcgacc aaaggtcgcc cgacgcccgg gctttgcccg ggcggcctca gtgagcgagc    120

gagcgcgcag                                                           130


<210> SEQ ID NO 5
<211> LENGTH: 242
<212> TYPE: DNA
<213> ORGANISM: Homo sapiens

<400> SEQUENCE: 5

actagtccgg atccaagctc agatctcgag ttgggcccca gaagcctggt ggttgtttgt     60

ccttctcagg ggaaaagtga ggcggcccct tggaggaagg ggccgggcag aatgatctaa    120

tcggattcca agcagctcag gggattgtct tttctagca ccttcttgcc actcctaagc    180

gtcctccgtg accccggctg ggatttagcc tggtgctgtg tcagccccgg gtcgacaagc    240

tt                                                                   242


<210> SEQ ID NO 6
<211> LENGTH: 225
<212> TYPE: DNA
<213> ORGANISM: Bos indicus

<400> SEQUENCE: 6

ctgtgccttc tagttgccag ccatctgttg tttgcccctc ccccgtgcct tccttgaccc     60

tggaaggtgc cactcccact gtcctttcct aataaaatga ggaaattgca tcgcattgtc    120

tgagtaggtg tcattctatt ctggggggtg gggtggggca ggacagcaag ggggaggatt    180

gggaagacaa tagcaggcat gctggggatg cggtgggctc tatgg                    225


<210> SEQ ID NO 7
<211> LENGTH: 3265
<212> TYPE: DNA
<213> ORGANISM: Artificial Sequence
<220> FEATURE:
<223> OTHER INFORMATION: Synthetic Expression cassette encoding human
      RPE65

<400> SEQUENCE: 7
```

```
ctctccaaga tccaacaaaa gtgattatac cccccaaaat atgatggtag tatcttatac     60
taccatcatt tttataggcat agggctctta gctgcaaata atggaactaa ctctaataaa   120
gcagaacgca aatattgtaa atattagaga gctaacaatc tctgggatgg ctaaaggatg   180
gagcttggag gctacccagc cagtaacaat attccgggct ccactgttga acggagacac   240
tacaactgcc ttggatgggc agagatatta tggatgctaa gccccaggtg ctaccattag   300
gacttctacc actgtcccta acgggtggag cccatcacat gcctatgccc tcactgtaag   360
gaaatgaagc tactgttgta tatcttggga agcacttgga ttaattgtta tacagttttg   420
ttgaagaaga cccctagggt aagtagccat aactgcacac taaatttaaa attgttaatg   480
agtttctcaa aaaaaatgtt aaggttgtta gctggtatag tatatatctt gcctgttttc   540
caaggacttc tttgggcagt accttgtctg tgctggcaag caactgagac ttaatgaaag   600
agtattggag atatgaatga attgatgctg tatactctca gagtgccaaa catataccaa   660
tggacaagaa ggtgaggcag agagcagaca ggcattagtg acaagcaaag atatgcagaa   720
tttcattctc agcaaatcaa aagtcctcaa cctggttgga agaatattgg cactgaatgg   780
tatcaataag gttgctagag agggttagag gtgcacaatg tgcttccata acattttata   840
cttctccaat cttagcacta atcaaacatg gttgaatagt ttgtttacta taactcttac   900
agagttataa gatctgtgaa gacagggaca gggacaatac ccatctctgt ctggttcata   960
ggtggtatgt aatagatatt tttaaaaata agtgagttaa tgaatgaggg tgagaatgaa  1020
ggcacagagg tattaggggg aggtgggccc cagagaatgg tgccaaggtc cagtggggtg  1080
actgggatca gctcaggcct gacgctggcc actcccacct agctcctttc tttctaatct  1140
gttctcattc tccttgggaa ggattgaggt ctctggaaaa cagccaaaca actgttatgg  1200
gaacagcaag cccaaataaa gccaagcatc agggggatct gagagctgaa agcaacttct  1260
gttccccctc cctcagctga aggggtgggg aagggctccc aaagccataa ctccttttaa  1320
gggatttaga aggcataaaa aggcccctgg ctgagaactt ccttcttcat tctgcagttg  1380
gtaatcacta gtaacggccg ccagcaagct tgaattcatg tctatccagg ttgagcatcc  1440
tgctggtggt tacaagaaac tgtttgaaac tgtggaggaa ctgtcctcgc cgctcacagc  1500
tcatgtaaca ggcaggatcc ccctctggct caccggcagt ctccttcgat gtgggccagg  1560
actctttgaa gttggatctg agccatttta ccacctgttt gatgggcaag ccctcctgca  1620
caagtttgac tttaaagaag gacatgtcac ataccacaga aggttcatcc gcactgatgc  1680
ttacgtacgg gcaatgactg agaaaaggat cgtcataaca gaatttggca cctgtgcttt  1740
cccagatccc tgcaagaata tattttccag gttttttttct tactttcgag gagtagaggt  1800
tactgacaat gcccttgtta atgtctaccc agtgggggaa gattactacg cttgcacaga  1860
gaccaacttt attacaaaga ttaatccaga gaccttggag acaattaagc aggttgatct  1920
ttgcaactat gtctctgtca atggggccac tgctcacccc cacattgaaa atgatggaac  1980
cgtttacaat attggtaatt gctttggaaa aaatttttca attgcctaca acattgtaaa  2040
gatcccacca ctgcaagcag acaaggaaga tccaataagc aagtcagaga tcgttgtaca  2100
attcccctgc agtgaccgat tcaagccatc ttacgttcat agttttggtc tgactcccaa  2160
ctatatcgtt tttgtggaga caccagtcaa aattaacctg ttcaagttcc tttcttcatg  2220
gagtctttgg ggagccaact acatggattg ttttgagtcc aatgaaacca tgggggtttg  2280
gcttcatatt gctgacaaaa aaaggaaaaa gtacctcaat aataaataca gaacttctcc  2340
```

```
tttcaacctc ttccatcaca tcaacaccta tgaagacaat gggtttctga ttgtggatct   2400

ctgctgctgg aaaggatttg agtttgttta taattactta tatttagcca atttacgtga   2460

gaactgggaa gaagtgaaaa aaaatgccag aaaggctccc caacctgaag ttaggagata   2520

tgtacttcct ttgaatattg acaaggctga cacaggcaag aatttagtca cgctccccaa   2580

tacaactgcc actgcaattc tgtgcagtga cgagactatc tggctggagc ctgaagttct   2640

cttttcaggg cctcgtcaag catttgagtt tcctcaaatc aattaccaga agtattgtgg   2700

gaaaccttac acatatgcgt atggacttgg cttgaatcac tttgttccag ataggctctg   2760

taagctgaat gtcaaaacta aagaaacttg ggtttggcaa gagcctgatt catacccatc   2820

agaacccatc tttgtttctc acccagatgc cttggaagaa gatgatggtg tagttctgag   2880

tgtggtggtg agcccaggag caggacaaaa gcctgcttat ctcctgattc tgaatgccaa   2940

ggacttaagt gaagttgccc gggctgaagt ggagattaac atccctgtca cctttcatgg   3000

actgttcaaa aaatcttgaa gcttggctga tcagcctcga ctgtgccttc tagttgccag   3060

ccatctgttg tttgcccctc ccccgtgcct tccttgaccc tggaaggtgc cactcccact   3120

gtcctttcct aataaaatga ggaaattgca tcgcattgtc tgagtaggtg tcattctatt   3180

ctggggggtg gggtggggca ggacagcaag ggggaggatt gggaagacaa tagcaggcat   3240

gctggggatg cggtgggctc tatgg                                         3265
```

```
<210> SEQ ID NO 8
<211> LENGTH: 1382
<212> TYPE: DNA
<213> ORGANISM: Homo sapiens

<400> SEQUENCE: 8

ctctccaaga tccaacaaaa gtgattatac cccccaaaat atgatggtag tatcttatac     60

taccatcatt ttataggcat agggctctta gctgcaaata atggaactaa ctctaataaa    120

gcagaacgca aatattgtaa atattagaga gctaacaatc tctgggatgg ctaaaggatg    180

gagcttggag gctacccagc cagtaacaat attccgggct ccactgttga acggagacac    240

tacaactgcc ttggatgggc agagatatta tggatgctaa gccccaggtg ctaccattag    300

gacttctacc actgtcccta acgggtggag cccatcacat gcctatgccc tcactgtaag    360

gaaatgaagc tactgttgta tatcttggga agcacttgga ttaattgtta tacagttttg    420

ttgaagaaga cccctagggt aagtagccat aactgcacac taaatttaaa attgttaatg    480

agtttctcaa aaaaaatgtt aaggttgtta gctggtatag tatatatctt gcctgttttc    540

caaggacttc tttgggcagt accttgtctg tgctggcaag caactgagac ttaatgaaag    600

agtattggag atatgaatga attgatgctg tatactctca gagtgccaaa catataccaa    660

tggacaagaa ggtgaggcag agagcagaca ggcattagtg acaagcaaag atatgcagaa    720

tttcattctc agcaaatcaa aagtcctcaa cctggttgga agaatattgg cactgaatgg    780

tatcaataag gttgctagag agggttagag gtgcacaatg tgcttccata acattttata    840

cttctccaat cttagcacta atcaaacatg gttgaatagt ttgtttacta taactcttac    900

agagttataa gatctgtgaa gacagggaca gggacaatac ccatctctgt ctggttcata    960

ggtggtatgt aatagatatt tttaaaaata agtgagttaa tgaatgaggg tgagaatgaa   1020

ggcacagagg tattaggggg aggtgggccc cagagaatgg tgccaaggtc cagtggggtg   1080

actgggatca gctcaggcct gacgctggcc actcccacct agctcctttc tttctaatct   1140

gttctcattc tccttgggaa ggattgaggt ctctggaaaa cagccaaaca actgttatgg   1200
```

```
gaacagcaag cccaaataaa gccaagcatc agggggatct gagagctgaa agcaacttct   1260

gttccccctc cctcagctga aggggtgggg aagggctccc aaagccataa ctccttttaa   1320

gggatttaga aggcataaaa aggcccctgg ctgagaactt ccttcttcat tctgcagttg   1380

gt                                                                  1382
```

<210> SEQ ID NO 9
<211> LENGTH: 1602
<212> TYPE: DNA
<213> ORGANISM: Homo sapiens

<400> SEQUENCE: 9

```
atgtctatcc aggttgagca tcctgctggt ggttacaaga aactgtttga aactgtggag     60

gaactgtcct cgccgctcac agctcatgta acaggcagga tccccctctg gctcaccggc    120

agtctccttc gatgtgggcc aggactcttt gaagttggat ctgagccatt ttaccacctg    180

tttgatgggc aagccctcct gcacaagttt gactttaaag aaggacatgt cacataccac    240

agaaggttca tccgcactga tgcttacgta cgggcaatga ctgagaaaag gatcgtcata    300

acagaatttg gcacctgtgc tttcccagat ccctgcaaga atatattttc caggtttttt    360

tcttactttc gaggagtaga ggttactgac aatgcccttg ttaatgtcta cccagtgggg    420

gaagattact acgcttgcac agagaccaac tttattacaa agattaatcc agagaccttg    480

gagacaatta agcaggttga tctttgcaac tatgtctctg tcaatggggc cactgctcac    540

ccccacattg aaaatgatgg aaccgtttac aatattggta attgctttgg aaaaaatttt    600

tcaattgcct acaacattgt aaagatccca ccactgcaag cagacaagga agatccaata    660

agcaagtcag agatcgttgt acaattcccc tgcagtgacc gattcaagcc atcttacgtt    720

catagttttg gtctgactcc caactatatc gtttttgtgg agacaccagt caaaattaac    780

ctgttcaagt tcctttcttc atggagtctt tggggagcca actacatgga ttgttttgag    840

tccaatgaaa ccatgggggt ttggcttcat attgctgaca aaaaaaggaa aaagtacctc    900

aataataaat acagaacttc tcctttcaac ctcttccatc acatcaacac ctatgaagac    960

aatgggtttc tgattgtgga tctctgctgc tggaaaggat ttgagtttgt ttataattac   1020

ttatatttag ccaatttacg tgagaactgg gaagaagtga aaaaaaatgc cagaaaggct   1080

ccccaacctg aagttaggag atatgtactt cctttgaata ttgacaaggc tgacacaggc   1140

aagaatttag tcacgctccc caatacaact gccactgcaa ttctgtgcag tgacgagact   1200

atctggctgg agcctgaagt tctcttttca gggcctcgtc aagcatttga gtttcctcaa   1260

atcaattacc agaagtattg tgggaaacct tacacatatg cgtatggact tggcttgaat   1320

cactttgttc cagataggct ctgtaagctg aatgtcaaaa ctaaagaaac ttgggtttgg   1380

caagagcctg attcataccc atcagaaccc atctttgttt ctcacccaga tgccttggaa   1440

gaagatgatg gtgtagttct gagtgtggtg gtgagcccag gagcaggaca aaagcctgct   1500

tatctcctga ttctgaatgc caaggactta agtgaagttg cccgggctga agtggagatt   1560

aacatccctg tcacctttca tggactgttc aaaaaatctt ga                       1602
```

<210> SEQ ID NO 10
<211> LENGTH: 2205
<212> TYPE: DNA
<213> ORGANISM: Artificial Sequence
<220> FEATURE:
<223> OTHER INFORMATION: VP1 coding sequence derived from AAV4

```
<400> SEQUENCE: 10

atgactgacg gttaccttcc agattggcta gaggacaacc tctctgaagg cgttcgagag     60

tggtgggcgc tgcaacctgg agcccctaaa cccaaggcaa atcaacaaca tcaggacaac    120

gctcggggtc ttgtgcttcc gggttacaaa tacctcggac ccggcaacgg actcgacaag    180

ggggaacccg tcaacgcagc ggacgcggca gccctcgagc acgacaaggc ctacgaccag    240

cagctcaagg ccggtgacaa cccctacctc aagtacaacc acgccgacgc ggagttccag    300

cagcggcttc agggcgacac atcgtttggg ggcaacctcg gcagagcagt cttccaggcc    360

aaaaagaggg ttcttgaacc tcttggtctg gttgagcaag cgggtgagac ggctcctgga    420

aagaagagac cgttgattga atccccccag cagcccgact cctccacggg tatcggcaaa    480

aaaggcaagc agccggctaa aaagaagctc gttttcgaag acgaaactgg agcaggcgac    540

ggacccccctg agggatcaac ttccggagcc atgtctgatg acagtgagat gcgtgcagca    600

gctggcggag ctgcagtcga gggcggacaa ggtgccgatg gagtgggtaa tgcctcgggt    660

gattggcatt gcgattccac ctggtctgag ggccacgtca cgaccaccag caccagaacc    720

tgggtcttgc ccacctacaa caaccacctc tacaagcgac tcggagagag cctgcagtcc    780

aacacctaca acggattctc cacccccctgg ggatactttg acttcaaccg cttccactgc    840

cacttctcac cacgtgactg gcagcgactc atcaacaaca actggggcat gcgacccaaa    900

gccatgcggg tcaaaatctt caacatccag gtcaaggagg tcacgacgtc gaacggcgag    960

acaacggtgg ctaataacct taccagcacg gttcagatct ttgcggactc gtcgtacgaa   1020

ctgccgtacg tgatggatgc gggtcaagag ggcagcctgc ctccttttcc caacgacgtc   1080

tttatggtgc cccagtacgg ctactgtgga ctggtgaccg gcaacacttc gcagcaacag   1140

actgacagaa atgccttcta ctgcctggag tactttcctt cgcagatgct gcggactggc   1200

aacaactttg aaattacgta cagttttgag aaggtgcctt tccactcgat gtacgcgcac   1260

agccagagcc tggaccggct gatgaaccct ctcatcgacc agtacctgtg ggactgcaa    1320

tcgaccacca ccggaaccac cctgaatgcc gggactgcca ccaccaactt taccaagctg   1380

cggcctacca acttttccaa ctttaaaaag aactggctgc ccgggccttc aatcaagcag   1440

cagggcttct caaagactgc caatcaaaac tacaagatcc ctgccaccgg gtcagacagt   1500

ctcatcaaat acgagacgca cagcactctg gacggaagat ggagtgccct gacccccgga   1560

cctccaatgg ccacggctgg acctgcggac agcaagttca gcaacagcca gctcatcttt   1620

gcggggcctg aacagaacgg caacacggcc accgtacccg ggactctgat cttcacctct   1680

gaggaggagc tggcagccac caacgccacc gatacggaca tgtggggcaa cctacctggc   1740

ggtgaccaga gcaacagcaa cctgccgacc gtggacagac tgacagcctt gggagccgtg   1800

cctggaatgg tctggcaaaa cagagacatt tactaccagg gtcccatttg ggccaagatt   1860

cctcataccg atggacactt tcacccctca ccgctgattg gtgggtttgg gctgaaacac   1920

ccgcctcctc aaatttttat caagaacacc ccggtacctg cgaatcctgc aacgaccttc   1980

agctctactc cggtaaactc cttcattact cagtacagca ctggccaggt gtcggtgcag   2040

attgactggg agatccagaa ggagcggtcc aaacgctgga accccgaggt ccagtttacc   2100

tccaactacg gacagcaaaa ctctctgttg tgggctcccg atgcggctgg gaaatacact   2160

gagcctaggg ctatcggtac ccgctacctc acccaccacc tgtaa                    2205

<210> SEQ ID NO 11
<211> LENGTH: 1797
```

<212> TYPE: DNA
<213> ORGANISM: Artificial Sequence
<220> FEATURE:
<223> OTHER INFORMATION: VP2 coding sequence derived from AAV4

<400> SEQUENCE: 11

```
acggctcctg gaaagaagag accgttgatt gaatcccccc agcagcccga ctcctccacg     60
ggtatcggca aaaaaggcaa gcagccggct aaaaagaagc tcgttttcga agacgaaact    120
ggagcaggcg acggaccccc tgagggatca acttccggag ccatgtctga tgacagtgag    180
atgcgtgcag cagctggcgg agctgcagtc gagggcggac aaggtgccga tggagtgggt    240
aatgcctcgg gtgattggca ttgcgattcc acctggtctg agggccacgt cacgaccacc    300
agcaccagaa cctgggtctt gcccacctac aacaaccacc tctacaagcg actcggagag    360
agcctgcagt ccaacaccta caacggattc tccaccccct ggggatactt tgacttcaac    420
cgcttccact gccacttctc accacgtgac tggcagcgac tcatcaacaa caactggggc    480
atgcgaccca aagccatgcg ggtcaaaatc ttcaacatcc aggtcaagga ggtcacgacg    540
tcgaacggcg agacaacggt ggctaataac cttaccagca cggttcagat ctttgcggac    600
tcgtcgtacg aactgccgta cgtgatggat gcgggtcaag agggcagcct gcctcctttt    660
cccaacgacg tctttatggt gccccagtac ggctactgtg gactggtgac cggcaacact    720
tcgcagcaac agactgacag aaatgccttc tactgcctgg agtactttcc ttcgcagatg    780
ctgcggactg gcaacaactt tgaaattacg tacagttttg agaaggtgcc tttccactcg    840
atgtacgcgc acagccagag cctggaccgg ctgatgaacc ctctcatcga ccagtacctg    900
tggggactgc aatcgaccac caccggaacc accctgaatg ccgggactgc caccaccaac    960
tttaccaagc tgcggcctac caacttttcc aactttaaaa agaactggct gcccgggcct   1020
tcaatcaagc agcagggctt ctcaaagact gccaatcaaa actacaagat ccctgccacc   1080
gggtcagaca gtctcatcaa atacgagacg cacagcactc tggacggaag atggagtgcc   1140
ctgacccccg gacctccaat ggccacggct ggacctgcgg acagcaagtt cagcaacagc   1200
cagctcatct ttgcggggcc tgaacagaac ggcaacacgg ccaccgtacc cgggactctg   1260
atcttcacct ctgaggagga gctggcagcc accaacgcca ccgatacgga catgtggggc   1320
aacctacctg gcggtgacca gagcaacagc aacctgccga ccgtggacag actgacagcc   1380
ttgggagccg tgcctggaat ggtctggcaa aacagagaca tttactacca gggtcccatt   1440
tgggccaaga ttcctcatac cgatggacac tttcacccct caccgctgat tggtgggttt   1500
gggctgaaac acccgcctcc tcaaattttt atcaagaaca ccccggtacc tgcgaatcct   1560
gcaacgacct tcagctctac tccggtaaac tccttcatta ctcagtacag cactggccag   1620
gtgtcggtgc agattgactg ggagatccag aaggagcggt ccaaacgctg gaaccccgag   1680
gtccagttta cctccaacta cggacagcaa aactctctgt tgtgggctcc cgatgcggct   1740
gggaaataca ctgagcctag ggctatcggt acccgctacc tcacccacca cctgtaa      1797
```

<210> SEQ ID NO 12
<211> LENGTH: 1617
<212> TYPE: DNA
<213> ORGANISM: Artificial Sequence
<220> FEATURE:
<223> OTHER INFORMATION: VP3 coding sequence derived from AAV4

<400> SEQUENCE: 12

```
atgcgtgcag cagctggcgg agctgcagtc gagggcggac aaggtgccga tggagtgggt     60
```

```
aatgcctcgg gtgattggca ttgcgattcc acctggtctg agggccacgt cacgaccacc    120

agcaccagaa cctgggtctt gcccacctac aacaaccacc tctacaagcg actcggagag    180

agcctgcagt ccaacaccta caacggattc tccaccccct ggggatactt tgacttcaac    240

cgcttccact gccacttctc accacgtgac tggcagcgac tcatcaacaa caactggggc    300

atgcgaccca aagccatgcg ggtcaaaatc ttcaacatcc aggtcaagga ggtcacgacg    360

tcgaacggcg agacaacggt ggctaataac cttaccagca cggttcagat ctttgcggac    420

tcgtcgtacg aactgccgta cgtgatggat gcgggtcaag agggcagcct gcctcctttt    480

cccaacgacg tctttatggt gccccagtac ggctactgtg gactggtgac cggcaacact    540

tcgcagcaac agactgacag aaatgccttc tactgcctgg agtactttcc ttcgcagatg    600

ctgcggactg gcaacaactt tgaaattacg tacagttttg agaaggtgcc tttccactcg    660

atgtacgcgc acagccagag cctggaccgg ctgatgaacc ctctcatcga ccagtacctg    720

tggggactgc aatcgaccac caccggaacc accctgaatg ccgggactgc caccaccaac    780

tttaccaagc tgcggcctac caacttttcc aactttaaaa agaactggct gcccgggcct    840

tcaatcaagc agcagggctt ctcaaagact gccaatcaaa actacaagat ccctgccacc    900

gggtcagaca gtctcatcaa atacgagacg cacagcactc tggacggaag atggagtgcc    960

ctgacccccg gacctccaat ggccacggct ggacctgcgg acagcaagtt cagcaacagc   1020

cagctcatct ttgcggggcc tgaacagaac ggcaacacgg ccaccgtacc cgggactctg   1080

atcttcacct ctgaggagga gctggcagcc accaacgcca ccgatacgga catgtggggc   1140

aacctacctg gcggtgacca gagcaacagc aacctgccga ccgtggacag actgacagcc   1200

ttgggagccg tgcctggaat ggtctggcaa aacagagaca tttactacca gggtcccatt   1260

tgggccaaga ttcctcatac cgatggacac tttcacccct caccgctgat tggtgggttt   1320

gggctgaaac acccgcctcc tcaaattttt atcaagaaca ccccggtacc tgcgaatcct   1380

gcaacgacct tcagctctac tccggtaaac tccttcatta ctcagtacag cactggccag   1440

gtgtcggtgc agattgactg ggagatccag aaggagcggt ccaaacgctg gaaccccgag   1500

gtccagttta cctccaacta cggacagcaa aactctctgt tgtgggctcc cgatgcggct   1560

gggaaataca ctgagcctag ggctatcggt acccgctacc tcacccacca cctgtaa      1617
```

```
<210> SEQ ID NO 13
<211> LENGTH: 2175
<212> TYPE: DNA
<213> ORGANISM: Artificial Sequence
<220> FEATURE:
<223> OTHER INFORMATION: VP1 coding sequence derived from AAV5

<400> SEQUENCE: 13

atgtcttttg ttgatcaccc tccagattgg ttggaagaag ttggtgaagg tcttcgcgag     60

tttttgggcc ttgaagcggg cccaccgaaa ccaaaaccca atcagcagca tcaagatcaa    120

gcccgtggtc ttgtgctgcc tggttataac tatctcggac ccggaaacgg tctcgatcga    180

ggagagcctg tcaacagggc agacgaggtc gcgcgagagc acgacatctc gtacaacgag    240

cagcttgagg cgggagacaa cccctacctc aagtacaacc acgcggacgc cgagtttcag    300

gagaagctcg ccgacgacac atccttcggg ggaaacctcg gaaaggcagt ctttcaggcc    360

aagaaaaggg ttctcgaacc ttttggcctg gttgaagagg gtgctaagac ggcccctacc    420

ggaaagcgga tagacgacca ctttccaaaa agaaagaagg ctcggaccga agaggactcc    480

aagccttcca cctcgtcaga cgccgaagct ggacccagcg gatcccagca gctgcaaatc    540
```

```
ccagcccaac cagcctcaag tttgggagct gatacaatgt ctgcgggagg tggcggccca    600

ttgggcgaca ataaccaagg tgccgatgga gtgggcaatg cctcgggaga ttggcattgc    660

gattccacgt ggatggggga cagagtcgtc accaagtcca cccgaacctg ggtgctgccc    720

agctacaaca accaccagta ccgagagatc aaaagcggct ccgtcgacgg aagcaacgcc    780

aacgcctact ttggatacag cacccccctgg gggtactttg actttaaccg cttccacagc    840

cactggagcc cccgagactg gcaaagactc atcaacaact actggggctt cagaccccgg    900

tccctcagag tcaaaatctt caacattcaa gtcaaagagg tcacggtgca ggactccacc    960

accaccatcg ccaacaacct cacctccacc gtccaagtgt ttacggacga cgactaccag   1020

ctgccctacg tcgtcggcaa cgggaccgag ggatgcctgc cggccttccc tccgcaggtc   1080

tttacgctgc cgcagtacgg ttacgcgacg ctgaaccgcg acaacacaga aaatcccacc   1140

gagaggagca gcttcttctg cctagagtac tttcccagca agatgctgag aacgggcaac   1200

aactttgagt ttacctacaa ctttgaggag gtgcccttcc actccagctt cgctcccagt   1260

cagaacctgt tcaagctggc caacccgctg gtggaccagt acttgtaccg cttcgtgagc   1320

acaaataaca ctggcggagt ccagttcaac aagaacctgg ccgggagata cgccaacacc   1380

tacaaaaact ggttcccggg gcccatgggc cgaacccagg gctggaacct gggctccggg   1440

gtcaaccgcg ccagtgtcag cgccttcgcc acgaccaata ggatggagct cgagggcgcg   1500

agttaccagg tgcccccgca gccgaacggc atgaccaaca acctccaggg cagcaacacc   1560

tatgccctgg agaacactat gatcttcaac agccagccgg cgaacccggg caccaccgcc   1620

acgtacctcg agggcaacat gctcatcacc agcgagagcg agacgcagcc ggtgaaccgc   1680

gtggcgtaca acgtcggcgg gcagatggcc accaacaacc agagctccac cactgccccc   1740

gcgaccggca cgtacaacct ccaggaaatc gtgcccggca gcgtgtggat ggagagggac   1800

gtgtacctcc aaggacccat ctgggccaag atcccagaga cgggggcgca ctttcacccc   1860

tctccggcca tgggcggatt cggactcaaa cacccaccgc ccatgatgct catcaagaac   1920

acgcctgtgc ccggaaatat caccagcttc tcggacgtgc ccgtcagcag cttcatcacc   1980

cagtacagca ccgggcaggt caccgtggag atggagtggg agctcaagaa ggaaaactcc   2040

aagaggtgga acccagagat ccagtacaca aacaactaca acgaccccca gtttgtggac   2100

tttgccccgg acagcaccgg ggaatacaga accaccagac ctatcggaac ccgatacctt   2160

acccgacccc tttaa                                                    2175
```

<210> SEQ ID NO 14
<211> LENGTH: 1767
<212> TYPE: DNA
<213> ORGANISM: Artificial Sequence
<220> FEATURE:
<223> OTHER INFORMATION: VP2 coding sequence derived from AAV5

<400> SEQUENCE: 14

```
acggccccta ccggaaagcg gatagacgac cactttccaa aaagaaagaa ggctcggacc     60

gaagaggact ccaagccttc cacctcgtca gacgccgaag ctggacccag cggatcccag    120

cagctgcaaa tcccagccca accagcctca agtttgggag ctgatacaat gtctgcggga    180

ggtggcggcc cattgggcga caataaccaa ggtgccgatg gagtgggcaa tgcctcggga    240

gattggcatt gcgattccac gtggatgggg gacagagtcg tcaccaagtc cacccgaacc    300

tgggtgctgc ccagctacaa caaccaccag taccgagaga tcaaaagcgg ctccgtcgac    360
```

```
ggaagcaacg ccaacgccta ctttggatac agcacccccct gggggtactt tgactttaac    420
cgcttccaca gccactggag cccccgagac tggcaaagac tcatcaacaa ctactggggc    480
ttcagacccc ggtccctcag agtcaaaatc ttcaacattc aagtcaaaga ggtcacggtg    540
caggactcca ccaccaccat cgccaacaac ctcacctcca ccgtccaagt gtttacggac    600
gacgactacc agctgcccta cgtcgtcggc aacgggaccg agggatgcct gccggccttc    660
cctccgcagg tctttacgct gccgcagtac ggttacgcga cgctgaaccg cgacaacaca    720
gaaaatccca ccgagaggag cagcttcttc tgcctagagt actttcccag caagatgctg    780
agaacgggca acaactttga gtttacctac aactttgagg aggtgccctt ccactccagc    840
ttcgctccca gtcagaacct gttcaagctg gccaacccgc tggtggacca gtacttgtac    900
cgcttcgtga gcacaaataa cactggcgga gtccagttca acaagaacct ggccgggaga    960
tacgccaaca cctacaaaaa ctggttcccg gggcccatgg gccgaaccca gggctggaac   1020
ctgggctccg gggtcaaccg cgccagtgtc agcgccttcg ccacgaccaa taggatggag   1080
ctcgagggcg cgagttacca ggtgcccccg cagccgaacg gcatgaccaa caacctccag   1140
ggcagcaaca cctatgccct ggagaacact atgatcttca acagccagcc ggcgaacccg   1200
ggcaccaccg ccacgtacct cgagggcaac atgctcatca ccagcgagag cgagacgcag   1260
ccggtgaacc gcgtggcgta caacgtcggc gggcagatgg ccaccaacaa ccagagctcc   1320
accactgccc ccgcgaccgg cacgtacaac ctccaggaaa tcgtgcccgg cagcgtgtgg   1380
atggagaggg acgtgtacct ccaaggaccc atctgggcca agatcccaga gacgggggcg   1440
cactttcacc cctctccggc catgggcgga ttcggactca aacacccacc gcccatgatg   1500
ctcatcaaga acacgcctgt gcccggaaat atcaccagct tctcggacgt gcccgtcagc   1560
agcttcatca cccagtacag caccgggcag gtcaccgtgg agatggagtg ggagctcaag   1620
aaggaaaact ccaagaggtg gaacccagag atccagtaca caaacaacta caacgacccc   1680
cagtttgtgg actttgcccc ggacagcacc ggggaataca gaaccaccag acctatcgga   1740
acccgatacc ttacccgacc cctttaa                                        1767
```

<210> SEQ ID NO 15
<211> LENGTH: 1599
<212> TYPE: DNA
<213> ORGANISM: Artificial Sequence
<220> FEATURE:
<223> OTHER INFORMATION: VP3 coding sequence derived from AAV5

<400> SEQUENCE: 15

```
atgtctgcgg gaggtggcgg cccattgggc gacaataacc aaggtgccga tggagtgggc     60
aatgcctcgg gagattggca ttgcgattcc acgtggatgg gggacagagt cgtcaccaag    120
tccacccgaa cctgggtgct gcccagctac aacaaccacc agtaccgaga gatcaaaagc    180
ggctccgtcg acggaagcaa cgccaacgcc tactttggat acagcacccc ctgggggtac    240
tttgacttta accgcttcca cagccactgg agcccccgag actggcaaag actcatcaac    300
aactactggg gcttcagacc ccggtccctc agagtcaaaa tcttcaacat tcaagtcaaa    360
gaggtcacgg tgcaggactc caccaccacc atcgccaaca acctcacctc caccgtccaa    420
gtgtttacgg acgacgacta ccagctgccc tacgtcgtcg gcaacgggac cgagggatgc    480
ctgccggcct tccctccgca ggtctttacg ctgccgcagt acggttacgc gacgctgaac    540
cgcgacaaca cagaaaatcc caccgagagg agcagcttct tctgcctaga gtactttccc    600
agcaagatgc tgagaacggg caacaacttt gagtttacct acaactttga ggaggtgccc    660
```

-continued

```
ttccactcca gcttcgctcc cagtcagaac ctgttcaagc tggccaaccc gctggtggac    720

cagtacttgt accgcttcgt gagcacaaat aacactggcg gagtccagtt caacaagaac    780

ctggccggga gatacgccaa cacctacaaa aactggttcc cggggcccat gggccgaacc    840

cagggctgga acctgggctc cggggtcaac cgcgccagtg tcagcgcctt cgccacgacc    900

aataggatgg agctcgaggg cgcgagttac caggtgcccc cgcagccgaa cggcatgacc    960

aacaacctcc agggcagcaa cacctatgcc ctggagaaca ctatgatctt caacagccag   1020

ccggcgaacc cgggcaccac cgccacgtac ctcgagggca acatgctcat caccagcgag   1080

agcgagacgc agccggtgaa ccgcgtggcg tacaacgtcg gcgggcagat ggccaccaac   1140

aaccagagct ccaccactgc ccccgcgacc ggcacgtaca acctccagga aatcgtgccc   1200

ggcagcgtgt ggatggagag ggacgtgtac ctccaaggac ccatctgggc caagatccca   1260

gagacggggg cgcactttca cccctctccg gccatgggcg gattcggact caaacaccca   1320

ccgcccatga tgctcatcaa gaacacgcct gtgcccggaa atatcaccag cttctcggac   1380

gtgcccgtca gcagcttcat cacccagtac agcaccgggc aggtcaccgt ggagatggag   1440

tgggagctca agaaggaaaa ctccaagagg tggaacccag agatccagta cacaaacaac   1500

tacaacgacc cccagtttgt ggactttgcc ccggacagca ccggggaata cagaaccacc   1560

agacctatcg gaacccgata ccttacccga ccccttaa                           1599
```

RECOMBINANT ADENO-ASSOCIATED VIRUS PARTICLE PURIFICATION COMPRISING AN AFFINITY PURIFICATION STEP

FIELD OF THE INVENTION

The invention relates to the field of purification of Adeno-Associated Virus particles (rAAVs). In particular, it relates to methods for obtaining purified recombinant Adeno-Associated Virus particles (rAAV). It also relates to purified rAAV particles and compositions thereof which are obtainable using said methods. It further relates to AAV plasmids, and host cells which have been transfected with said plasmids, and also rAAV particles produced by said host cells.

BACKGROUND OF THE INVENTION

Gene delivery is a promising method for the treatment of acquired and inherited diseases. A number of viral-based systems for gene transfer purposes have been described, including Adeno-Associated Virus (AAV)-based systems. AAV is a helper-dependent DNA parvovirus that belongs to the genus Dependovirus. AAV requires co-infection with an unrelated helper virus, e.g., adenovirus, herpes virus, or vaccinia, in order for a productive infection to occur. In the absence of a helpervirus, AAV establishes a latent state by inserting its genome into a host cell chromosome. Subsequent infection by a helper virus rescues the integrated viral genome, which can then replicate to produce infectious viral progeny.

AAV has a wide host range and is able to replicate in cells from any species in the presence of a suitable helper virus. For example, human AAV will replicate in canine cells co-infected with a canine adenovirus. AAV has not been associated with any human or animal disease and does not appear to alter the biological properties of the host cell upon integration. For a review of AAV, see, e.g., Berns and Bohenzky (1987) Advances in Virus Research (Academic Press, Inc.) 32:243-307.

Le meur et al. ("*Restoration of vision in RPE*65-*deficient Briard dogs using an AAV serotype* 4 *vector that specifically targets the retinal pigmented epithelium*"; Gene Therapy; Vol. 14, 292-303; 2007) teaches the use of an rAAV for restoring vision in a RPE65-deficient Dog.

Petit et al. ("*Restoration of vision in the pde*6β-*deficient Dog, a Large Animal Model of Rod-cone Dystrophy*"; Molecular Therapy"; Vol. 20, no. 11, 2019-2030"; 2012) teaches the use of a rAAV for restoring vision in a PDE6β-deficient Dog.

For all those reasons, the use of Adeno-Associated Virus for gene therapy has been proposed. However, applications are still lacking due to the requirement for preparations having sufficient purity and/or infectivity for clinical use.

Thus, there remains a need for novel methods for purifying Adeno-Associated Virus particles (rAAVs). In particular, there remains a need for scalable methods which are well-defined, reproducible, and within controlled environmental conditions in accordance with Good Manufacturing Practices (GMP).

In particular, there remains a need for methods for purifying Adeno-Associated Virus particles (rAAVs) which require a limited number of steps.

There also remains a need for methods for purifying Adeno-Associated Virus particles (rAAVs) which are suitable for use as a medicament, and/or gene therapy.

Thus, there remains a need for scalable methods for purifying rAAV particles and compositions thereof, with high purity and infectivity.

Methods for purifying Adeno-Associated Virus particles have been reported in the prior Art. However, those methods are not necessarily satisfying for producing rAAV particles which are directly suitable for use as a medicament and/or for gene therapy.

WO2011/094198 teaches a method for purifying AAV particles, including a step of Ion Exchange Column Chromatography and a step of Tangential Flow Filtration.

WO03/097797 teaches a method for purifying virus particles with reduced contaminating DNA levels, which may include steps of cell lysis, depth filtration and/or centrifugation, ultracentrifugation, nuclease treatment, anion exchange chromatography and tangential flow filtration.

On the other hand, many of the available techniques have the disadvantage to require prior extensive treatment of the cell extracts, including density gradient, treatment with nucleases and detergents before the chromatography step. Such additional treatments render the whole process less satisfactory at an industrial scale.

Immunoaffinity chromatography has been reported as a fast, one-step purification method, for purifying adeno-associated viruses (AAV). However, its use is still limited, due to the highly specific nature of antibodies, or fragments thereof, when immobilized onto a chromatography support. What is more, immunoaffinity chromatography supports, when used for one-step purification methods, can be prone to generate a purified rAAV contaminated by a large proportion of empty particles and thus hinder its use for direct administration in gene therapy.

Peptide affinity purification has been reported as an alternative to immunoaffinity, or antibody-based affinity chromatography.

Pulicherla et al. ("Peptide affinity reagents for AAV capsid recognition and purification"; Gene Ther.; 18(10):1020-1024; 2011) reports a method for purifying AAV8 capsids which comprises a step of peptide affinity purification using a Pep8-based peptide, followed by an anion-exchange chromatography. However the method has the disadvantage of being restricted to AAV8 capsids, and requires significant optimization for producing clinical grade rAAV particles preparations.

In particular, peptide affinity purification requires to isolate and characterize novel peptide ligands and to generate a GMP chromatography column-compatible with these ligands; a step that may be time-consuming and expansive, and thus a bottleneck for scalability of the whole process.

Thus there remains a need for novel methods that can be scaled up with respect to good manufacturing practice issues, which remain acceptable from an economic point of view, and suitable for use as a medicament or for gene therapy.

There also remains a need for methods for purifying rAAV particles from a starting material containing rAAV particles belonging to a plurality of serotypes.

There also remains a need for methods for purifying rAAV particles with Immunoaffinity chromatography, with reduced empty particles into the purified rAAV particles.

There also remains a need for novel purified rAAV particles and compositions thereof, as such and/or for use as a medicament or for gene therapy, which can be further purified by said processes, and which remain suitable for producing rAAV particles in a given host cell.

SUMMARY OF THE INVENTION

The present invention relates to a method for obtaining purified recombinant Adeno-Associated Virus particles (rAAV), comprising the steps of:

a) performing a depth filtration of a starting material previously obtained from cells producing rAAV particles, the said starting material being selected in a group comprising a cell lysate and a culture supernatant, whereby a rAAV-containing clarified composition is provided;

b) submitting the rAAV-containing clarified composition to an affinity purification step, whereby a first rAAV enriched composition is provided;

c) submitting the first rAAV enriched composition at least once to:

c1) a step of anion-exchange chromatography on a chromatographic support wherein elution is performed by using a salt gradient, preferably a linear salt gradient, and wherein the rAAV-containing fraction is collected, whereby a second rAAV enriched composition is provided; or c2) a step of density gradient centrifugation, wherein the rAAV-containing fraction is collected, whereby a second rAAV enriched composition is provided;

d) submitting the second rAAV enriched composition to a step of tangential flow filtration, whereby purified recombinant Adeno-Associated Virus particles (rAAV) are provided.

In particular, the present invention relates to a method for obtaining purified recombinant Adeno-Associated Virus particles (rAAV), comprising the steps of:

a) performing a depth filtration of a starting material previously obtained from cells producing rAAV particles, the said starting material being selected in a group comprising a cell lysate and a culture supernatant, whereby a rAAV-containing clarified composition is provided;

b) submitting the rAAV-containing clarified composition to an immunoaffinity purification step, whereby a first rAAV enriched composition is provided;

c) submitting the first rAAV enriched composition at least once to:

c1) a step of anion-exchange chromatography on a chromatographic support wherein elution is performed by using a salt gradient, preferably a linear salt gradient, and wherein the rAAV-containing fraction is collected, whereby a second rAAV enriched composition is provided; or c2) a step of density gradient centrifugation, wherein the rAAV-containing fraction is collected, whereby a second rAAV enriched composition is provided;

d) submitting the second rAAV enriched composition to a step of tangential flow filtration, whereby purified recombinant Adeno-Associated Virus particles (rAAV) are provided.

The invention also relates to purified rAAV particles that are obtained by performing the method described above. It further relates to a purified rAAV particle composition comprising at least one purified rAAV particle as defined above.

It further relates to said purified rAAV particles and to compositions thereof, for use for gene therapy and/or for the preparation of a medicament for use for gene therapy.

The invention also relates to an AAV plasmid comprising an expression cassette encoding human PDE6-beta, and to a host cell transfected with said AAV plasmid, and further to rAAV particles which are produced by said host cell.

DETAILED DESCRIPTION OF THE INVENTION

Figure 1A:
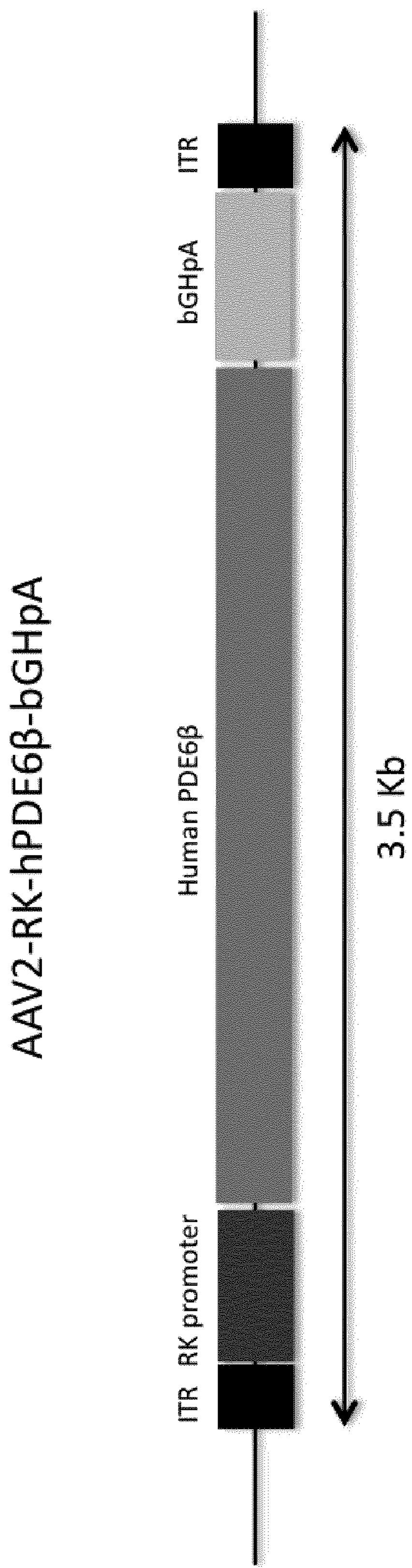
FIG. 1A: Cartography of the expression cassette of an AAV plasmid encoding human PDE6β. The nucleic acid sequence coding for the human PDE6β protein is associated at its 5' end to a human rhodopsine kinase (RK) promoter and at its 3' end to a bovine growth hormone polyadenylation site (bGHpA), flanked by Inverted Terminal Repeat (ITR) sequences.

The invention addresses the aforementioned needs.

The current invention provides a recombinant Adeno-Associated Virus (rAAV) particle purification method that includes two unique features that distinguish it from current "industry-standard" scalable AAV particles purification processes: 1) a modular platform process that can be used for purification of different AAV serotypes/capsid variants with high purity, and which is suitable for producing preparations directly suitable for clinical applications; and 2) a unique sequence of process steps, including an affinity chromatography (Immunoaffinity or peptide affinity chromatography) followed by at least one density gradient centrifugation step, or at least one anion-exchange chromatography preferably performed by using a linear salt gradient.

Surprisingly those characteristics confer unexpected scalability, for purifying a starting material such as a cell lysate or a culture supernatant. In particular, this process has the advantage of being suitable for optimization, in order to prepare purified recombinant Adeno-Associated Virus particles having optimal infectiosity, and which are suitable for gene therapy.

The use of one or more additional steps, including anion-chromatography steps and/or density gradient centrifugation, leads to optimal separation of empty and full particles on said support, and is thus suitable for isolating rAAV particles in an improved manner.

Advantageously, this multi-step purification method allows to purify clinical-grade rAAV preparations at an industrial scale.

Advantageously, the composition can be passed through the anion-exchange chromatography support using a linear salt gradient. Without wishing to be bound by any particular theory, the inventors are also of the opinion that the linear salt gradient provides more efficient separation of the eluted species, compared to step salt gradients. The difference lies in the lower slope of the gradient, which allows for the formation of a slow increase in salt concentration, and thus optimal separation of rAAV particles within the chromatography support.

To the best of the knowledge of the inventors, it is the first described "industry-standard" method for purifying clinical-grade rAAV particles, in particular rAAV particles belonging to the AAV4 serotype, which involves a multi-step purification method comprising an affinity chromatography step, in particular an immunoaffinity chromatography step.

Indeed, previously reported methods for purifying rAAV particles involved one-step affinity or immunoaffinity chromatography steps, and/or were not "industry-standard" methods.

Also, the methods of the invention are particularly suitable for purifying particular serotypes of rAAVs, due to the higher proportion of full particles in the final product.

Also, residual DNA at the end of the process is in accordance with clinical standards, even in the absence of treatment with detergents and nucleases, including DNAses.

Thus, the invention relates to a method for obtaining purified recombinant Adeno-Associated Virus particles (rAAV), and is particularly suitable for purifying rAAV particles belonging to a AAV serotype selected in a group comprising, or consisting of, AAV1, AAV2, AAV3, AAV4, AAV5, AAV8, AAV9, AAV10, and rhesus macaque-derived serotypes including AAVrh10, and mixtures thereof; in particular AAV4.

The present invention relates to a method for obtaining purified recombinant Adeno-Associated Virus particles (rAAV), comprising the steps of:

a) performing a depth filtration of a starting material previously obtained from cells producing rAAV particles, the said starting material being selected in a group comprising a cell lysate and a culture supernatant, whereby a rAAV-containing clarified composition is provided;

b) submitting the rAAV-containing clarified composition to an affinity purification step, whereby a first rAAV enriched composition is provided;

c) submitting the first rAAV enriched composition at least once to:

c1) a step of anion-exchange chromatography on a chromatographic support wherein elution is performed by using a salt gradient, preferably a linear salt gradient, and wherein the rAAV-containing fraction is collected, whereby a second rAAV enriched composition is provided; or c2) a step of density gradient centrifugation, wherein the rAAV-containing fraction is collected, whereby a second rAAV enriched composition is provided;

d) submitting the second rAAV enriched composition to a step of tangential flow filtration, whereby purified recombinant Adeno-Associated Virus particles (rAAV) are provided.

An affinity purification step may consist of a peptide affinity purification step or an immunoaffinity purification step.

According to a first embodiment, the invention relates to a method for obtaining purified recombinant Adeno-Associated Virus particles (rAAV), comprising the steps of:

a) performing a depth filtration of a starting material previously obtained from cells producing rAAV particles, the said starting material being selected in a group comprising a cell lysate and a culture supernatant, whereby a rAAV-containing clarified composition is provided;

b) submitting the rAAV-containing clarified composition to an immunoaffinity purification step, whereby a first rAAV enriched composition is provided;

c) submitting the first rAAV enriched composition at least once to:

c1) a step of anion-exchange chromatography on a chromatographic support wherein elution is performed by using a salt gradient, preferably a linear salt gradient, and wherein the rAAV-containing fraction is collected, whereby a second rAAV enriched composition is provided; or c2) a step of density gradient centrifugation, wherein the rAAV-containing fraction is collected, whereby a second rAAV enriched composition is provided;

d) submitting the second rAAV enriched composition to a step of tangential flow filtration, whereby purified recombinant Adeno-Associated Virus particles (rAAV) are provided.

The starting material may comprise either rAAV particles belonging to one serotype, or belonging to a plurality of serotypes, including rAAV particles belonging to the AAV4, AAV2, AAV10 and/or AAV5 serotype.

In particular, the starting material may comprise either rAAV particles belonging to one serotype, or belonging to a plurality of serotypes, including rAAV particles belonging to the AAV4 and/or AAV5 serotype.

Preferably, the invention relates to a method for obtaining purified recombinant Adeno-Associated Virus particles (rAAV) belonging to the AAV4 serotype, comprising the steps of:

a) performing a depth filtration of a starting material previously obtained from cells producing said rAAV4 particles belonging to the AAV4 serotype, the starting material being selected in a group comprising a cell lysate and a culture supernatant, whereby a rAAV-containing clarified composition is provided;

b) submitting the rAAV4-containing clarified composition to an immunoaffinity purification step, whereby a first rAAV4 enriched composition is provided;

c) submitting the first rAAV4 enriched composition at least once to c1) a step of anion-exchange chromatography on a chromatographic support wherein elution is performed by using a salt gradient, preferably a linear salt gradient, and wherein the rAAV-containing fraction is collected, whereby a second rAAV enriched composition is provided; or c2) a step of density gradient centrifugation, wherein the rAAV-containing fraction is collected, whereby a second rAAV4 enriched composition is provided;

d) submitting the second rAAV4 enriched composition to a step of tangential flow filtration, whereby purified recombinant Adeno-Associated Virus particles (rAAV) belonging to the AAV4 serotype are provided.

The purified rAAV particles of the invention comprise a heterologous nucleic acid encoding a desirable gene product. Such products include without limitation, siRNAs, antisense molecules, miRNAs, ribozymes and the like. Other products include nucleic acids encoding hormones, growth receptors, ligands and proteins useful for gene therapy.

According to a second embodiment, the invention relates to a purified rAAV particle obtained by performing the method as described above, and to compositions thereof.

According to a third embodiment, the invention relates to said purified rAAV particles and to compositions thereof, for use for gene therapy.

According to a fourth embodiment, the invention relates to an AAV plasmid comprising an expression cassette encoding human PDE6-beta, to a host cell which has been transfected with said AAV plasmid, and to rAAV particles produced by the host cell, as such and also for use for gene therapy.

According to the invention, the expression "comprising", such as in "comprising the steps of", is also understood as "consisting of", such as in "consisting of the steps of".

Methods for Obtaining Purified Recombinant Adeno-Associated Virus Particles

The invention relates to a method for obtaining purified recombinant Adeno-Associated Virus particles (rAAV), comprising the steps of:

a) performing a depth filtration of a starting material previously obtained from cells producing rAAV particles, the said starting material being selected in a group comprising a cell lysate and a culture supernatant, whereby a rAAV-containing clarified composition is provided;

b) submitting the rAAV-containing clarified composition to an affinity purification step, such as an immunoaffinity purification step or a peptide affinity purification step, whereby a first rAAV enriched composition is provided;

c) submitting the first rAAV enriched composition at least once to:

c1) a step of anion-exchange chromatography on a chromatographic support wherein elution is performed by using a salt gradient, preferably a linear salt gradient, and wherein the rAAV-containing fraction is collected, whereby a second rAAV enriched composition is provided; or c2) a step of density gradient centrifugation, wherein the rAAV-containing fraction is collected, whereby a second rAAV enriched composition is provided;

d) submitting the second rAAV enriched composition to a step of tangential flow filtration, whereby purified recombinant Adeno-Associated Virus particles (rAAV) are provided.

In particular, the affinity purification step is an immunoaffinity purification step.

More particularly, the invention relates to a method for obtaining purified recombinant Adeno-Associated Virus particles (rAAV), comprising the steps of:

a) performing a depth filtration of a starting material previously obtained from cells producing rAAV particles, the said starting material being selected in a group comprising a cell lysate and a culture supernatant, whereby a rAAV-containing clarified composition is provided;

b) submitting the rAAV-containing clarified composition to an immunoaffinity purification step, whereby a first rAAV enriched composition is provided;

c) submitting the first rAAV enriched composition at least once to:

c1) a step of anion-exchange chromatography on a chromatographic support wherein elution is performed by using a salt gradient, preferably a linear salt gradient, and wherein the rAAV-containing fraction is collected, whereby a second rAAV enriched composition is provided; or c2) a step of density gradient centrifugation, wherein the rAAV-containing fraction is collected, whereby a second rAAV enriched composition is provided;

d) submitting the second rAAV enriched composition to a step of tangential flow filtration, whereby purified recombinant Adeno-Associated Virus particles (rAAV) are provided.

According to some embodiments the method does include a step of treatment with detergents and/or nucleases, including DNAses.

According to some embodiments, the method does not include a step of treatment with detergents and/or nucleases, including DNAses.

According to another embodiment, the rAAV particles belong to a AAV serotype selected in a group comprising AAV1, AAV2, AAV3, AAV4, AAV5, AAV8, AAV9, AAV10, and rhesus macaque-derived serotypes including AAVrh10 and mixtures thereof; in particular AAV4.

According to one alternative embodiment, the rAAV particles consist of rAAV5 particles containing DNA comprising an expression cassette encoding human PDE6-beta.

According to said embodiment, the said expression cassette is of SEQ ID NO 1.

According to one embodiment, the rAAV5 particles contain a DNA comprising SEQ ID NO 2.

According to another alternative embodiment, the rAAV particles consist of rAAV4 particles containing DNA comprising an expression cassette encoding human RPE65.

The terms "recombinant AAV virion", "rAAV virion", "AAV particle", "full capsids" and "full particles" are defined herein as an infectious, replication-defective virus including an AAV protein shell, encapsidating a heterologous nucleotide sequence of interest which is flanked on both sides by AAV ITRs. A rAAV virion is produced in a suitable host cell which has had sequences specifying an AAV plasmid, AAV helper functions and accessory functions introduced therein. In this manner, the host cell is rendered capable of encoding AAV polypeptides that are required for packaging the AAV plasmid (containing a recombinant nucleotide sequence of interest) into infectious recombinant virion particles for subsequent gene delivery.

By "recombinant virus" is meant a virus that has been genetically altered, e.g., by the addition or insertion of a heterologous nucleic acid construct into the particle.

By "AAV virion" is meant a complete virus particle, such as a wild-type (wt) AAV virus particle (comprising a linear, single-stranded AAV nucleic acid genome associated with an AAV capsid protein coat). In this regard, single-stranded AAV nucleic acid molecules of either complementary sense, e.g., "sense" or "antisense" strands, can be packaged into any one AAV virion and both strands are equally infectious.' The term "host cell" denote, for example, microorganisms, yeast cells, insect cells, and mammalian cells, that can be, or have been, used as transitory or permanent stable producer cell lines recipients of an AAV helper construct, an AAV plasmid, an accessory function plasmid, or other transfer DNA. The term includes the progeny of the original cell which has been transfected. Thus, a "host cell" as used herein generally refers to a cell which has been transfected with an exogenous DNA sequence. It is understood that the progeny of a single parental cell may not necessarily be completely identical in morphology or in genomic or total DNA complement as the original parent, due to natural, accidental, or deliberate mutation.

The term "rAAV-containing clarified composition" encompasses any composition including rAAV particles, which is obtained after a step of depth-filtration of a starting material such as a cell lysate or a culture supernatant. A "rAAV-containing clarified composition" is distinct from a "rAAV enriched composition" and/or purified rAAV particles.

Thus, a "rAAV-containing clarified composition" may encompass any composition including rAAV particles which derives directly from a depth-filtered starting material such as a cell lysate or a culture supernatant, and which has not been further submitted to a step of enrichment and/or purification, including which has not been submitted to a step of ion (e.g. cation)-exchange chromatography.

According to said embodiment, the invention relates to a method for obtaining purified recombinant Adeno-Associated Virus particles (rAAV), comprising the steps of:

a) performing a depth filtration of a cell lysate and/or a culture supernatant, whereby a rAAV-containing clarified composition is provided;

b) submitting the rAAV-containing clarified composition to an affinity purification step, such as an immunoaffinity purification step or a peptide affinity purification step, whereby a first rAAV enriched composition is provided;

c) submitting the first rAAV enriched composition at least once to c1) a step of anion-exchange chromatography on a chromatographic support wherein elution is performed by using a salt gradient, preferably a linear salt gradient, and wherein the rAAV-containing fraction is collected, whereby a second rAAV enriched composition is provided; or c2) a step of density gradient centrifugation, wherein the rAAV-containing fraction is collected, whereby a second rAAV enriched composition is provided;

d) submitting the second rAAV enriched composition to a step of tangential flow filtration, whereby purified recombinant Adeno-Associated Virus particles (rAAV) are provided.

According to another embodiment, the invention relates to a method for obtaining purified recombinant Adeno-Associated Virus particles (rAAV) of the invention, wherein the rAAV-containing clarified composition that is submitted to the first step of affinity step (immunoaffinity purification step or peptide affinity purification step), is the composition obtained directly at the end of step a). Thus, according to said embodiment, steps a) and b) are consecutive steps.

By "consecutive step" is meant any step that comes after a first step, for which any inbetween step of chromatography step, in particular ion (cation)-exchange chromatography, is excluded. On the other hand, and unless stated otherwise, "consecutive steps" do not exclude buffer exchange and/or dilution steps, for the purpose of modifying buffer conditions (i.e. concentration of salt; pH) of said compositions.

According to an embodiment, the method of the invention does not comprise a cation-exchange chromatography step.

According to an embodiment, the method of the invention does not comprise an apatite chromatography step.

According to one preferred embodiment, the invention relates to a method for obtaining purified recombinant Adeno-Associated Virus particles (rAAV) of the invention, wherein affinity purification (immunoaffinity or peptide affinity purification) and anion-exchange chromatography steps, or alternatively affinity purification (immunoaffinity or peptide affinity purification) and density gradient centrifugation, are consecutive steps. Thus, according to said embodiment, steps b) and c) are consecutive steps.

According to another embodiment, steps c) and d) are consecutive.

According to another embodiment, steps b) and c) and d) are consecutive.

According to another embodiment, steps a) and b) and c) are consecutive.

According to another embodiment, steps a) and b) and c) and d) are consecutive.

Thus, the invention also relates to a method for obtaining purified recombinant Adeno-Associated Virus particles (rAAV), comprising the steps of:

a) performing a depth filtration of a starting material previously obtained from cells producing rAAV particles, the said starting material being selected in a group comprising a cell lysate and a culture supernatant, whereby a rAAV-containing clarified composition is provided;

b) submitting the rAAV-containing clarified composition obtained at step a) to an affinity purification step (immunoaffinity or peptide affinity purification step), whereby a first rAAV enriched composition is provided;

c) submitting the first rAAV enriched composition obtained at step b) at least once to:

c1) a step of anion-exchange chromatography on a chromatographic support wherein elution is performed by using a salt gradient, preferably a linear salt gradient, and wherein the rAAV-containing fraction is collected, whereby a second rAAV enriched composition is provided; or c2) a step of density gradient centrifugation, wherein the rAAV-containing fraction is collected, whereby a second rAAV enriched composition is provided;

d) submitting the second rAAV enriched composition obtained at step c) to a step of tangential flow filtration, whereby purified recombinant Adeno-Associated Virus particles (rAAV) are provided.

According to another embodiment, steps a) and b) and c) and d) are consecutive and the starting material in step a) is directly obtained from a cell lysate or a culture supernatant.

According to said embodiment, the invention relates to a method for obtaining purified recombinant Adeno-Associated Virus particles (rAAV), comprising the steps of:

a) performing a depth filtration of a cell lysate and/or a culture supernatant, whereby a rAAV-containing clarified composition is provided;

b) submitting the rAAV-containing clarified composition obtained at step a) to an affinity purification step (immunoaffinity or peptide affinity purification step), whereby a first rAAV enriched composition is provided;

c) submitting the first rAAV enriched composition obtained at step b) at least once to c1) a step of anion-exchange chromatography on a chromatographic support wherein elution is performed by using a salt gradient, preferably a linear salt gradient, and wherein the rAAV-containing fraction is collected, whereby a second rAAV enriched composition is provided; or c2) a step of density gradient centrifugation, wherein the rAAV-containing fraction is collected, whereby a second rAAV enriched composition is provided;

d) submitting the second rAAV enriched composition obtained at step c) to a step of tangential flow filtration, whereby purified recombinant Adeno-Associated Virus particles (rAAV) are provided.

The above-mentioned methods all include at least: 1) one step of depth filtration of a starting material; 2) a first step of affinity (immunoaffinity or peptide affinity) chromatography; 3) a second step of anion-exchange chromatography or density gradient centrifugation; and 4) a step of tangential flow filtration. Each individual step will be further defined herebelow.

The inventors are also of the opinion that each additional step contributes to the scalability and high purity of the purified recombinant Adeno-Associated virus particles.

Depth filtration

Depth filtration step allows for discarding a major part of contaminant DNA and proteins. This step renders possible the purification of rAAV particles through immunoaffinity chromatography directly from a rAAV-containing clarified composition.

According to one embodiment, the starting material used at step a) is a cell lysate obtained by contacting a culture of cells producing rAAV particles with a composition comprising at least a detergent or a surfactant, and preferably a detergent.

According to one embodiment, the starting material used at step a) is a cell lysate obtained by contacting a culture of cells producing rAAV particles with a composition which may or may not comprise a detergent or a surfactant, but which is not treated with a nuclease such as a DNAse.

Examples of suitable detergents for cell lysis include Triton X-100, Triton X-114, NP-40, Brij-35, Brij-58, Tween 20, Tween 80, Octyl glucoside, Octyl thioglucoside, SDS, CHAPS and CHAPSO.

According to one preferred embodiment, step a) is performed by using a depth filter membrane comprising a layer of borosilicate glass microfibers and a layer of mixed esters of cellulose.

According to one exemplary embodiment, step a) is performed using a Polysep™ II (Millipore®) filter.

Affinity Chromatography

The term "affinity chromatography" or "affinity purification" as used herein designates any method that uses specific binding interactions between molecules. A particular ligand is chemically immobilized or "coupled" to a solid support so that when a complex mixture is passed over the column, those molecules having specific binding affinity to the ligand become bound. After other sample components are washed away, the bound molecule is stripped from the support, resulting in its purification from the original sample.

The term "immunoaffinity chromatography" as used herein designates any method that uses immobilized antibodies, or fragments thereof, in affinity chromatography.

The term "antibodies or fragments thereof" may include monoclonal and polyclonal antibodies, naturally and non-naturally occurring antibodies, whole antibodies and fragments thereof, including fragment antigen-binding such as Fv, Fab and $F(ab')_2$ regions, complementarity determining regions (CDRs), single-domain antibodies, nanobodies, and mixtures thereof.

The term "fragment thereof" may encompass any fragment of an antibody that can be obtained by deleting part of the original antibody, including in a non-limitative manner any antibody of which the Fc region or parts of the variable region (including CDRs) have been deleted.

The term "peptide affinity chromatography" as used herein designates any method that uses immobilized peptide in affinity chromatography. Peptide affinity chromatography is well known in the art (see for example Pulicherla et al. 2011. Gen Ther 18(10): 1020-1024).

When immobilized onto the chromatography support, the term encompasses any of the aforementioned variants as long as it retains its ability to bind to at least one epitope at the surface of the rAAV particles which are purified.

In particular, such antibodies or fragments thereof may include isotypes of the IgA, IgD, IgE, IgG and IgM subclasses.

According to one particular embodiment, the antibodies or fragments thereof are monoclonal.

Antibodies which are considered by the invention may be naturally-occurring or non-naturally occurring. They may be of human or non-human origin.

According to one exemplary embodiment, the antibodies are single-chain antibodies, such as the ones obtained by immunization of camelids including dromedaries, camels, llamas, and alpacas; or sharks.

Antibodies and fragments thereof may be obtained and immobilized onto supports by using a variety of techniques that range from covalent attachment to adsorption-based methods, as described for instance in Moser & Hage («Immunoaffinity chromatography: an introduction to applications and recent developments»; Bioanalysis; 2(4): 769-790; 2010).

Monoclonal antibodies may be prepared using any technique which provides for the production of antibody molecules by continuous cell lines in culture. These include, but are not limited to, the hybridoma technique, the human B-cell hybridoma technique, and the EBV-hybridoma technique (Kohler, et al., 1975, Nature 256:495-497; Kozbor, et at, 1985, J. Immunol. Methods 81:31-42; Cote, et al., 1983, Proc. Natl. Acad. Sci. 80:2026-2030; Cole, et al, 1984, MoL Cell Biol. 62:109-120).

A number of suitable immunoaffinity chromatography supports for use with the present invention are known and include without limitation, Affi-Gel (Biorad); Affinica Agarose/Polymeric Supports (Schleicher and Schuell); AvidGel (BioProbe); Bio-Gel (BioRad); Fractogel (EM Separations); HEMA-AFC (Alltech); Reacti-Gel (Pierce); Sephacryl (Pharmacia); Sepharose (Pharmacia); Superose (Pharmacia); Trisacryl (IBF); TSK Gel Toyopearl (TosoHaas); Ultragel (IBF); AvidGel CPG (BioProbe); HiPAC (ChromatoChem); Protein-Pak Affinity Packing (Waters); Ultraffinity-EP (Bodman) and Emphaze (3M Corp./Pierce).

Other chromatography supports include affinity monolith chromatography supports, and POROS® affinity chromatography supports.

Preferably, antibodies and fragments thereof may be immobilized on an agarose matrix.

Thus, according to one embodiment, the method comprises a step b) that is performed by using a chromatography support onto which antibodies or fragments thereof directed to the said rAAV particles, are immobilized.

In particular the antibodies or fragments thereof are immobilized to an agarose matrix by a hydrophilic spacer arm.

According to one embodiment, step b) is performed using an antibody that binds specifically to at least one epitope that is present on the AAV particles. In one embodiment, said epitope belongs at least to serotypes selected in a group comprising AAV1, AAV2, AAV3, AVV4, AAV5, AAV6, AAV7, AAV8, AAV9 and AAVrh10.

In one embodiment, said epitope belongs at least to serotypes selected in a group comprising or consisting of AAV1, AAV2, AAV3 and AAV5.

According to one particular embodiment, step b) is performed using a single-chain camelid antibody, or VHH antibody, that binds specifically to at least one epitope that is present on the AAV particles. In one embodiment, said epitope belongs at least to serotypes selected in a group comprising AAV1, AAV2, AAV3, AVV4, AAV5, AAV6, AAV7, AAV8, AAV9 and AAVrh10, which includes an epitope selected from the group comprising or consisting of: AAV1, AAV2, AAV3 and AAV5.

Still, according to one exemplary embodiment, step b) is performed using an AVB Sepharose™ chromatography (GE Healthcare) support.

According to one preferred embodiment, the pH of the rAAV-containing clarified composition, in particular the rAAV4, rAAVrh0 or rAAV2-containing clarified composition, is at a neutral to basic pH, prior to loading on the Immunoaffinity column, which includes a pH ranging from 6.0 to 8.0.

According to one most preferred, the rAAV-containing clarified composition is a rAAV4-containing clarified composition.

Still, according to one exemplary embodiment, a rAAV-containing clarified composition is loaded on an AVB column equilibrated with Dulbecco's Phosphate Buffered Saline (DPBS) supplemented with Calcium and Magnesium, or Phosphate Buffered Saline (PBS).

Still, according to one exemplary embodiment, the first rAAV enriched composition is eluted from the Immunoaffinity column with an acid pH. An acid pH may refer to any pH below 7.0, including below 5.0, or even below 3.0.

According to said exemplary embodiment, the first rAAV enriched composition is eluted from the Immunoaffinity column with an acid pH, wherein said pH is below 3.0, which includes a pH of about 2.0.

The above-mentioned immunoaffinity supports and methods are particularly convenient in methods of the invention, for purifying rAAV particles belonging to the AAV4, AAV10 (i.e. AAVrh10) or AAV2 serotype; in particular rAAV particles belonging to the AAV4 serotype.

Once eluted, the pH of the first rAAV enriched composition is preferably neutralized in a manner suitable for obtaining a first rAAV enriched composition with a neutral or basic pH, which includes a pH of 8.0 or above, which includes 8.5. The reason is that rAAV particles, including rAAV4 particles, tend to lose their integrity and/or infectivity if maintained in a composition having an acid pH.

According to one exemplary embodiment, the first rAAV enriched composition is neutralized in a Tris buffer having a pH of about 8.5.

According to another exemplary embodiment, the first rAAV enriched composition is neutralized in a Tris buffer having a pH of about 8.0.

Advantageously, before, during or after neutralization, the first rAAV enriched composition can be supplemented with a non-ionic surfactant, for example Pluronic® F68 (Gibco).

The non-ionic surfactant can be present in an amount ranging from 0.0001% to 0.1% (v/v) of the total volume of the composition; which includes in an amount ranging from 0.0005% to 0.005% (v/v) of the total volume of the composition; which includes about 0.001% (v/v) of the total volume of the composition.

Advantageously the Adeno-Associated Virus particles (rAAV) enriched composition is concentrated in the presence of a non-ionic surfactant, for example Pluronic® F-68 (Gibco), and in amount as defined above.

Also advantageously the Adeno-Associated Virus particles (rAAV) containing composition is diafiltered and concentrated against a Saline Ocular Solution, which may further comprise a non-ionic surfactant, as defined above, and in an amount as also defined above.

The use of a non-ionic surfactant, as defined above, and in the other steps, further contributes to the efficiency and scalability of the method. In particular, the use of a non-ionic surfactant, as defined above, prevents the aggregation or adherence of rAAV particles, before, during and after purification.

Anion-Exchange chromatography A number of suitable anion exchangers for use with the present invention are known and include without limitation, MACRO PREP Q (strong anion-exchanger available from BioRad, Hercules, Calif.); UNOSPHERE Q (strong anion-exchanger available from BioRad, Hercules, Calif.); POROS 50HQ (strong anion-exchanger available from Applied Biosystems, Foster City, Calif.); POROS 50D (weak anion-exchanger available from Applied Biosystems, Foster City, Calif.); POROS 50PI (weak anion-exchanger available from Applied Biosystems, Foster City, Calif.); SOURCE 30Q (strong anion-exchanger available from GE Healthcare, N.J.); DEAE SEPHAROSE (weak anion-exchanger available from GE Healthcare, Piscataway, N.J.); Q SEPHAROSE (strong anion-exchanger available from GE Healthcare Biosciences, Piscataway, N.J.), Capto Q and Capto Adhere (GE Healthcare, N.J.).

Examples of suitable monolithic chromatographic supports are known in the Art, and include in a non-limitative manner the monolithic column CIMmultus® QA, CIM® QA, CIM DEAE and CIMmultus® DEAE (Bia Separations).

Chromatography monoliths are one-piece porous solids made of fused micrometer-sized globules of silica or an organic polymer that can be synthesized directly inside a chromatography tube. This makes this support very resistant and ready-to-use, with no package parameters variability.

Monoliths are homogenous columns with a continuous porous bed matrix, consisting of interconnected perfusion channels. These channels are relatively large (1-5 μm) by comparison to the typical pore sizes of packed-bed particle-based chromatography (5-100 nm). One benefit of this is that it increases the potential binding capacity of macromolecules such as virus because of high surface of accessibility. These supports generate low counter pressure even at high flow rates, and low shear rate.

By comparison to packed-bed columns, the improved mass transport of monolithic supports results in efficient separation of the macromolecules.

From a practical point of view, the use of these columns allows to work with a viral product (even when it is a cellular lysate) at high flow rate compared to packed-bed columns, with a high binding capacity and a good resolution, independent of the flow rate. The high resolution of these supports contributes to the reduction of the purification steps and the scalability of the whole process.

According to some embodiments, the method for obtaining purified recombinant Adeno-Associated Virus particles (rAAV) comprises only one anion-exchange chromatography step.

According to some embodiments, the method for obtaining purified recombinant Adeno-Associated Virus particles (rAAV) comprises more than one anion-exchange chromatography step, which includes in particular two, three or even four anion-chromatography steps. When the method comprises more than one anion-exchange chromatography step, the aforementioned steps may be achieved on the same type of support or on different supports.

According to an exemplary embodiment, the at least one chromatographic support at step c1) is a monolithic chromatographic support.

The anion exchange column is first equilibrated using standard buffers and according to the manufacturer's specifications. For example, the column can be equilibrated with, e.g., a 5 to 50 mM, preferably 7-20 mM, such as 20 mM, Tris buffer. Sample is then loaded and two elution buffers are used, one low salt buffer and one high salt buffer.

Fractions are collected following a progressive mix of the low salt and high salt buffers, generating a salt gradient, and the eluted material is detected in the fractions using standard techniques, such as monitoring UV absorption at 260 and 280 nm. Using an anion exchanger, the protein peaks from the lower salt eluate contain AAV empty capsids and the higher salt fractions contain AAV particles.

In particular, on the anion exchange column, AAV particles can be further purified using an appropriate buffer at a pH of from about pH 5 to pH 12, preferably pH 6 to pH 10, and even more preferably pH 7 to pH 9.5, such as pH 7.1, 7.2, 7.3, 7.4-8.0, 8.1, 8.2, 8.3, 8.4, 8.5-9.0, 9.1, 9.2, 9.3, 9.4, 9.5, or any pH between the stated ranges.

Appropriate buffers for use with the anion exchange columns are well known in the art and are generally cationic or zwitterionic in nature. Such buffers include, without limitation, buffers with the following buffer ions: N-methylpiperazine; piperazine; Bis-Tris; Bis-Tris propane; Triethanolamine; Tris; N-methyldiethanolamine; 1,3-diaminopropane; ethanolamine; acetic acid, and the like. To elute the sample, the ionic strength of the starting buffer is increased using a salt, such as NaCl, KCl, sulfate, formate or acetate, at an appropriate pH.

Advantageously, all the buffers used during, before or after the anion-exchange chromatography comprise a non-ionic surfactant, for example Pluronic® F-68 (ThermoFisher Scientific), in an amount ranging from 0.0001% to 0.1% (v/v) of the total volume of the buffer composition; which includes in an amount ranging from 0.0005% to 0.005% (v/v) of the total volume of the buffer composition; which includes about 0.001% (v/v) of the total volume of the buffer composition.

The nature of the resins used (i.e. strong or weak ion exchangers) and the conditions of salt concentration, buffer used, and pH, will vary on the AAV capsid variant (i.e. AAV capsid serotype or pseudotype). While the known AAV capsid variants all share features such as size and shape, they differ in fine details of molecular topology and surface charge distribution. Hence, while all capsid variants are expected to be amenable to purification by anion exchange chromatography, and relevant methods can be determined in a systematic manner using chromatography resin and buffer screening experiments, different conditions will be required for each AAV capsid variant to achieve efficient AAV particle purification. The determination for such conditions is readily apparent to the skilled artisan.

Advantageously, at the end of step b), the pH of the rAAV-containing clarified composition is adjusted at a basic pH so as to ensure optimal retention of the rAAV particles on the at least one anion-chromatography support used at step c).

A pH of 8.5, or above 8.5, which includes 9, is particularly convenient for the binding of rAAV4 particles, or rAAV4-containing clarified compositions, to the anion-exchange column.

Thus, according to one exemplary embodiment, at the end of step b), the optimal pH of a rAAV4-containing clarified composition for binding to the anion-exchange column is adjusted to pH 8.5, or above 8.5, which includes 9.

A pH of 8.5, or above 8.5, which includes 9, is particularly convenient for the binding of rAAVrh10 particles, or rAAVrh0-containing clarified compositions, to the anion-exchange column.

Thus, according to one exemplary embodiment, at the end of step b), the optimal pH of a rAAVrh10-containing clarified composition for binding to the anion-exchange column is adjusted to pH 8.5, or above 8.5, which includes 9.

A pH of 8.5, or above 8.5, which includes 9, is particularly convenient for the binding of rAAV2 particles, or rAAV2-containing clarified compositions, to the anion-exchange column.

Thus, according to one exemplary embodiment, at the end of step b), the optimal pH of a rAAV2-containing clarified composition for binding to the anion-exchange column is adjusted to pH 8.5, or above 8.5, which includes 9.

Appropriate buffers for use with the anion exchange columns are well known in the art and are generally cationic or zwitterionic in nature. Such buffers include, without limitation, buffers with the following buffer ions: N-methylpiperazine; piperazine; Bis-Tris; Bis-Tris propane; Triethanolamine; Tris; N-methyldiethanolamine; 1,3-diaminopropane; ethanolamine; acetic acid, and the like. To elute the sample, the ionic strength of the starting buffer is increased using a salt, such as NaCl, KCl, sulfate, formate or acetate, at an appropriate pH.

Prior to elution, the anion-exchange chromatography may also include an optional step of treating the support, or anion-exchange column, with a lower salt concentration than what is generally used for the elution step. Such treatment may also be referred herein as a "pre-elution" step.

Thus, in one embodiment of the invention, the anion exchange column is first treated with a low salt concentration, e.g., 5-100 mM of salt, in particular 5-100 mM of NaCl, such as 5, 10, 15, 20, 25, 30, 35, 40, 45, 50, 55, 60, 65-100 mM, or any concentration within these ranges. For example the salt concentration in a "first pre-elution step" may initially correspond to the salt concentration of the buffer used for binding the rAAV particles to the column after loading.

In some embodiments, and following initial treatment, the column is then treated with a higher salt concentration in order to elute impurities, such as a higher NaCl concentration, or with another buffer with a greater ionic strength. One example for use as the second buffer is a sodium acetate buffer or a Tris-based buffer. This additional step may also be referred herein as a "second pre-elution" step. In that case, one may take care that the salt concentration remains low enough to not elute the AAV particles from the column.

After additional impurities are eluted from the column, the AAV particles can then be recovered using a higher concentration of salt in the elution step.

In some embodiments, the elution pH on the chromatographic support is adjusted depending on the rAAV particle that is purified. Elution at an optimal pH has the advantage of maintaining optimal infectivity of a given particle.

Elution of rAAV particles from the chromatographic support at step c), in particular elution of rAAV4 particles, can also be adjusted at pH 8.

Preferably, elution of rAAV particles from the chromatographic support is performed by using a linear salt gradient. The salt may be selected from the group consisting of: NaCl, KCl, sulfate, formate and acetate; and preferably NaCl.

The term "slope of the linear salt gradient" refers to the slope between two points (A,B) of the linear gradient, and depends both on the concentration of salt in the chromatography support and the column volume (CV) that is eluted over time, according to the following formula:

$$\text{slope }(A,B)=(\text{concentration of salt in }B-\text{concentration of salt in }A)/(\text{column volume in }B-\text{column volume in }A).$$

Thus, the slope of the linear salt gradient can be expressed in M/CV or in mM/CV, and is preferably a shallow salt gradient according to standard protocols.

According to one embodiment, the slope of the linear salt gradient in step c) is equal or less than 0.1 M/CV, in particular ranging from 0.015 to 0.09 M/CV.

According to one embodiment, the slope of the linear salt gradient in step c) is equal or less than 0.07 M/CV, in particular ranging from 0.01 to 0.06 M/CV.

Advantageously, the method may include an additional step of dilution of the rAAV enriched composition before or after the anion-exchange chromatography step. A step of dilution may be, for instance, in the form of a buffer exchange step.

According to one preferred embodiment, at the end of step c), the second rAAV enriched composition is stored under a frozen form until its use for performing step d).

Density gradient centrifugation.

In density gradient centrifugation, the density of the suspension medium varies in a known manner from one end of the density gradient container, e.g of the centrifuge tube, to the other end. When the particle under the influence of centrifugal force reaches the point of its isopycnic density, i.e., when the density of the surrounding liquid is equal to the density of the rAAV particle, the rAAV particle will cease to migrate along the force vector.

Solute systems used to establish density gradients for centrifugation which are considered by the invention include, in a non-limitative manner, inorganic salts (cesium chloride, potassium bromide, sodium chloride), sucrose and several commercially available solutes such as Ficoll®, a synthetic polysaccharide made by crosslinking sucrose; Percoll™, a suspension of silica particles coated with polyvinylpyrrolidone; and Nycodenz®, a derivative of the synthetic molecule metrizoic acid (metrizamide). Iodixinol, or Iodixanol, a dimer of Nycodenz®, is also used widely.

Thus, step c) may include a step of submitting the first rAAV enriched composition obtained at step b) at least once to a step of density gradient centrifugation, wherein the rAAV-containing fraction is collected, whereby a second rAAV enriched composition is provided;

According to one embodiment, a step of density gradient centrifugation is selected from: cesium chloride (CsCl) gradient centrifugation; iodixanol gradient centrifugation; sucrose gradient centrifugation; Percoll™ gradient centrifugation; Ficoll® gradient centrifugation; and most preferably cesium chloride (CsCl) gradient centrifugation.

Advantageously, prior to density-gradient based centrifugation, the first rAAV enriched composition may be precipitated in order to obtain a suitable volume of material for performing the density gradient centrifugation step, in particular in the presence of Polyethylene Glycol, such as PEG 8000.

It may also be diafiltered and concentrated by Tangential Flow Filtration (TFF).

Thus, according to one embodiment, the first rAAV enriched composition is precipitated, in the presence of PEG 8000, for instance PEG 8000 at a final concentration of about 5 to 10% (w/v). Additionally, the sample can then be centrifugated prior to density-gradient based centrifugation, so as to facilitate the collection of the precipitated rAAV particles for their further processing.

According to a most general embodiment, density gradient-based centrifugation methods comprise at least the steps of:

i) providing a density-gradient forming solution which includes the sample of interest;

ii) centrifuging the solution provided at step (i) in a manner suitable for producing a density gradient having at least one layer comprising a second rAAV enriched composition;

iii) optionally recovering the layer comprising the second rAAV enriched composition.

Accordingly, the sample of interest may comprise, or may consist of, the first rAAV enriched composition.

According to the invention, a “density-gradient forming solution” is a solution which is either in the form of a continuous or discontinuous gradient prior to centrifugation; or alternatively for which the gradient is self-formed during centrifugation.

A “density-gradient forming solution” may be selected from the group consisting of a cesium chloride (CsCl), Iodixanol, sucrose, Percoll™, and Ficoll® solution; and most preferably cesium chloride (CsCl) solution or Iodixanol.

Iodixanol is preferred, including for reglementary reasons.

In some embodiments of Step i), the sample of interest may be simply in admixture with the density gradient forming solution.

In some other embodiments of Step i), the sample of interest may be layered on the top of the density gradient forming solution, i.e. at the interface between the said gradient forming solution and the atmosphere.

Step ii) of centrifuging the solution in a manner suitable for producing a density gradient having at least one layer comprising a second rAAV enriched composition can thus be achieved by centrifuging a density-gradient forming solution which is either in the form of a continuous or discontinuous gradient prior to centrifugation; or alternatively for which the gradient is self-formed during centrifugation.

According to said embodiment, the solution provided at step (i) can already be in the form of a continuous or discontinuous gradient of density. For instance, the solution provided at step (i) can be in the form of a set of layers having, from the top to the bottom, a plurality of layers having increasing densities.

The preparation of continuous and discontinuous density gradients is well known in the Art.

According to another embodiment, the density-gradient forming solution provided at step (i) can be a solution, for instance an isopycnic solution, of which the density gradient is self-formed during centrifugation.

According to said embodiment, the density gradient can be formed during the step (ii) of centrifuging. For instance the formation of a density gradient during centrifugation may occur by starting from an isopycnic Cesium Chloride (CsCl) solution.

According to one embodiment, the AAV-containing solution provided at step (i) is a CsCl solution having a density ranging from about 1 to 1.6 g/cm$^3$, which includes 1, 1.1, 1.2, 1.3, 1.4, and 1.5 to 1.6 g/cm$^3$, which includes 1.3 to 1.5 g/cm$^3$, which includes 1.376 g/cm$^3$.

According to one embodiment, the sample of interest at step (i) is present at the top layer of the said solution before centrifugation.

Step ii) of centrifuging the solution is known in the Art and consists of applying a centrifugal field to said solution, at least until a gradient has formed from top to bottom.

The centrifugal force is generally applied by spinning a centrifuge tube containing the solution of step (i) for a given time (i.e. a few hours), for a given intensity (estimated in round per minutes or rpm; or alternatively in g) and at a given temperature in a centrifuge rotor.

One example of a preferred protocol is described in Example 1.

Another example of a preferred protocol is described in Example 2.

According to one embodiment, the rotor used at step (ii) is a SW41 rotor.

According to one embodiment, step ii) consists of centrifuging the solution provided at step (i) in a SW41 rotor at about 30,000 to 50,000 rpm, which includes 38,000 rpm, for about 24 to 72 hours, which includes 48 hours, and at a temperature ranging from about 4° C. to 20° C. in temperature, which includes 15° C., in order to separate full particles from “empty” ones. The layer comprising the second rAAV enriched composition can be recovered at step (iii) based on the banding density of purified rAAVs.

The determination of banding densities of purified rAAVs is also known in the Art and can be determined either by comparison to a reference value or empirically.

The density of rAAV particles can be expressed in g/cm$^3$.

For reference, densities of known rAAV particles, either full or empty, are described in Qu et al (“Separation of adeno-associated virus type 2 empty particles from genome containing vectors by anion-exchange column chromatography; Journal of Virological Methods; 2006): ≈1.32 g/mL for empty capsids, 1.40 g/mL for genome containing capsids.

Overall densities for one given preparation may depend both on the serotype of the rAAV, and the presence of full or empty particles in the preparation.

In particular, the resolution of the resulting gradient will depend upon various parameters, including in a non-limitative manner the nature of the solution used at step (i), the parameters used at step (ii) for centrifuging the solution and the banding densities of rAAVs which have to be recovered.

For instance, Iodixanol is an iodinated density gradient medium which is known in the Art and used for clinical use. Because the apparent density of macromolecules in iodixanol is different from that in CsCl, the banding density of purified rAAVs must be determined empirically. For rAAV capsids, density is of about 1.40 g/mL in CsCl and 1.266 g/mL in Iodixanol.

At step (iii), and after fractionation of the gradient, the positive fractions can also be identified by quantitative PCR, and optionally pooled.

Optionally, the rAAV particles-containing fractions can also be concentrated and/or dialyzed further, for instance using the Tangential Flow Filtration.

Optionally, the rAAV particles-containing fractions can also be submitted to an additional density gradient centrifugation.

Protocols for purifying rAAV particles preparations using density gradient centrifugation are known in the Art, and are further described, for instance, in Zolotukhin et al. («Recombinant adeno-associated virus purification using novel methods improves infectious titer and yield»; Gene Therapy (1999).

Tangential Flow Filtration and Subsequent Steps

Tangential Flow Filtration is a polishing step which allows to discard small-sized particle-related impurities through cycles of concentration and diafiltration through the pores of the filter. This polishing step has the other advantage of being suitable for changing the buffer of the eluted fractions and for concentrating the rAAVs.

Tangential Flow Filtration is achieved preferably using, as a filter, a hollow fiber filter.

According to one embodiment, step d) is performed by using a filter membrane having a molecular weight cut-off value equal or inferior to 150 kDa, in particular ranging from 20 kDa to 150 kDa, preferably 25 kDa to 150 kDa, which includes about 30 kDa.

The man skilled in the Art will recognize that the molecular weight cut-off must be adjusted depending on the type of rAAV particle that is purified and on the of elution parameters (pH, salt).

According to some embodiment, salts and/or detergents and/or surfactants and/or nucleases can added during, before or after the Tangential Flow Filtration, in particular during or before the Tangential Flow Filtration.

According to one embodiment, the method may further include a step of treatment with detergents, surfactants, and/or nucleases, including DNAses, during, before or after the Tangential Flow Filtration.

Advantageously the Adeno-Associated Virus particles (rAAV) containing composition is diafiltered and concentrated in the presence of a non-ionic surfactant, for example Pluronic® F-68 (Gibco).

The non-ionic surfactant can be present in an amount ranging from 0.0001% to 0.1% (v/v) of the total volume of the composition; which includes in an amount ranging from 0.0005% to 0.005% (v/v) of the total volume of the composition; which includes about 0.001% (v/v) of the total volume of the composition.

Also advantageously the Adeno-Associated Virus particles (rAAV) containing composition is diafiltered and concentrated against a Saline Ocular Solution, which may further comprise a non-ionic surfactant as defined above, and in an amount as also described above.

According to one embodiment, the purified recombinant Adeno-Associated Virus particles (rAAV) obtained at step c) or d) are submitted to an additional gradient, including a step of differential centrifugation, including density gradients, in particular selected from: cesium chloride (CsCl) gradient centrifugation; iodixanol gradient centrifugation; sucrose gradient centrifugation.

According to one preferred embodiment, the method may further include an additional step of Tangential Flow Filtration after said additional gradient.

According to one embodiment, the purified recombinant Adeno-Associated Virus particles (rAAV) obtained at step d) are sterilized.

According to one embodiment, the purified recombinant Adeno-Associated Virus particles (rAAV) are submitted to a step of sterile filtration over a filter membrane having a pore size of 0.2 μm or less.

The invention also relates to purified rAAV particles obtained by performing a method as defined above.

Characterization of the purified rAAV particles

Advantageously, the above-mentioned method can be used for obtaining purified recombinant Adeno-Associated Virus particles (rAAV) which are suitable for gene therapy, and/or for preparing a medicament for gene therapy.

According to one preferred embodiment, said purified rAAV particles are suitable for use for gene therapy.

The purity of adeno-associated virus (AAV) particles preparations also has important implications for both safety and efficacy of clinical gene transfer.

The method used to purify a rAAV particle can dramatically influence the purity of the preparation in terms of the amount of host cell protein contamination and of ratio of full/total particles.

Vector particle concentration can be assessed by quantitative PCR (genome containing particles) or by ELISA (total vector particles) as shown in Example 1

The purity of the preparation, is most commonly assessed by sodium dodecyl sulfate-polyacrylamide gel electrophoresis (SDS-PAGE), as shown in Example 1.

Bands corresponding to the viral structural (capsid) proteins, VP1, VP2 and VP3 may be visualized after staining and their size and relative intensity assessed with respect to contaminating proteins. For reference, VP1, VP2 and VP3 belonging to the AAV4 and AAV5 serotypes are encoded by nucleic acids of sequences SEQ ID NO 10 to 15.

VP1, VP2, and VP3 belonging to the AAV4 serotype can be encoded respectively by nucleic acids of sequences SEQ ID NO 10 to 12.

VP1, VP2, and VP3 belonging to the AAV5 serotype can be encoded respectively by nucleic acids of sequences SEQ ID NO 13 to 15.

The above-mentioned sequences are given as references.

Thus, the term "purity" refers to the absence of general impurities. Purity is expressed as a percentage, and relates to the total amount of VP1, VP2 and VP3 proteins, in comparison to the total amount of detected proteins in a Coomassie Blue stained polyacrylamide gel.

The term "general impurities" refers to impurities which were present in the starting material but which are not considered as particle-related impurities. Thus, general impurities encompass impurities which are derived from the host cells but which are not AAV particles.

The term "particle-related impurities" refers to all types of AAV particles other than bona fide recombinant AAV particles. Particle-related impurities include empty AAV capsids (also referred to as "empties", or "empty particles", and AAV particles containing polynucleotide sequences other than the intended particle genome (also referred to "AAV-encapsidated nucleic acid impurities" or "AAV-encapsidated DNA impurities").

Residual DNA or Host Cell DNA can be present as contaminants in rAAV preparations. Because residual DNA can have negative effects, manufacturers must ensure that final products derived from host cells contain acceptable levels of residual DNA.

Residual DNA testing can be assessed by quantitative PCR, including real-time PCR, using the protocol described in Example 1. Residual DNA is expressed in ng per mL, or alternatively in ng per dose.

Preferably, residual DNA is determined by qPCR by determining the relative quantity of an E1A amplicon DNA in the composition, in comparison to a standard curve established with a known amount of E1A amplicon DNA.

A «dose» is defined as the volume of preparation which corresponds to $1*10^{12}$ vector genome (vg).

Advantageously, compositions of the invention can be further characterized by their ratio of empty rAAV particles/full rAAV particles.

The terms "empty capsid" and "empty particle" refer to an AAV virion that includes an AAV protein shell but that lacks in whole or part the polynucleotide construct comprising the heterologous nucleotide sequence of interest flanked on both sides by AAV ITRs. Accordingly, the empty capsid does not function to transfer the gene of interest into the host cell.

The ratio of empty rAAV particles/full rAAV particles can be assessed by SDS-PAGE Gel, using the protocol described in Example 1.

Infectious particle concentration can also be assessed using the protocol of ICA described in Example 1.

Thus, a composition of the invention comprises at least one purified rAAV particle using either one of the above mentioned methods, and preferably has at least one of the following characteristics:

- a purity equal or superior to 90%, and preferably superior to 99%; or even 100%;
- an amount of residual cellular DNA equal or inferior to 50 ng per dose.

An amount of residual cellular DNA equal or inferior to 50 ng per dose includes equal or inferior to 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, or 5 ng per dose.

In particular, a composition of the invention comprises at least one purified rAAV particle using either one of the above mentioned methods, and has the following characteristics:

- a purity equal or superior to 99%; or even 100%; and
- an amount of residual cellular DNA equal or inferior to 25 ng per dose, which includes 15 ng per dose.

Most preferably, the purity of the composition is superior to 99%, which includes a purity of 100%.

According to a preferred embodiment, a purified rAAV particle composition of the invention is a composition comprising rAAV particles purified according to the invention, optionally supplemented with a non-ionic surfactant.

According to a preferred embodiment, a purified rAAV particle composition of the invention is a Saline Ocular Solution comprising rAAV particles purified according to the invention, optionally supplemented with a non-ionic surfactant.

According to an exemplary embodiment, the composition is obtained directly from one of the above-mentioned methods.

Saline Ocular Solutions which are suitable for the invention may be obtained from BD Medical, such as for example BD Standard Solution or BD Aqueo Premium™).

According to said exemplary embodiment, the non-ionic surfactant is preferably Pluronic® F-68 (Gibco®).

The non-ionic surfactant (i.e. Pluronic® F-68) can be present in an amount ranging from 0.0001% to 0.1% (v/v) of the total volume of the composition; which includes in an amount ranging from 0.0005% to 0.005% (v/v) of the total volume of the composition; which includes about 0.001% (v/v) of the total volume of the composition.

Compositions of the invention, including compositions for administration and/or of use for gene therapy, as further described herebelow are preferably sterile.

rAAV Particles for Use for Gene Therapy

The invention further relates to a method for obtaining purified recombinant Adeno-Associated Virus particles (rAAV), for use for gene therapy and/or for use for the preparation of a medicament suitable for gene therapy.

Advantageously, such rAAV particles and compositions thereof are also suitable, as such, for use for gene therapy, and/or for use for the preparation of a medicament suitable for gene therapy.

By "gene therapy" is meant the administration of a nucleic acid sequence to an individual, for treating and/or preventing and/or reducing the likelihood of the occurrence of a disease. Several approaches have been proposed in the Art. In view of the above, rAAV particles are used as vehicles for delivering said nucleic acid sequence to the individual to be treated.

One may replace a mutated gene that causes disease with a healthy copy of the gene.

One may inactivate ("knocking-out") a mutated gene that is functioning improperly.

One may introduce a new gene into the body for treating and/or preventing and/or reducing the likelihood of the occurrence of a disease.

The reported methods and plasmids are particularly efficient for use for preparing a medicament for eye-diseases, including sight loss, and more particularly rod-cone dystrophies due to rod-specific defects.

In particular, said disease may be selected from phosphodiesterase 6 (PDE6)-related diseases, including PDE6β-related diseases, and Retinal Pigment Epithelium-specific 65 kDa protein (RPE65)-related diseases.

RPE65-related diseases include Leber's congenital amaurosis and retinitis pigmentosa. PDE6-related diseases include Rod-cone Dystrophy, and retinitis pigmentosa The individual to be treated includes humans and non-human mammals.

AAV particles and compositions thereof may be administered topically or parenterally, which includes intraorbital and intraocular administration. Intraocular administration further includes intravitreal, subretinal and intracorneal administration.

Thus, compositions comprising said AAV particles are preferably suitable for topical or parenteral administration, which includes intraocular, (preferably intravitreal and subretinal), and intracorneal administration.

rAAV particles of the invention preferably include an expression cassette encoding human PDE6β, or human RPE65 gene, respectively of sequences SEQ ID NO 1 and 7, and as further described herebelow.

According to one preferred embodiment, a purified rAAV particle can be obtained by performing any one of the methods described herein. A purified rAAV particle composition comprises at least one of said purified rAAV particles. Purified rAAV particles and compositions thereof are suitable for use for gene therapy.

AAV Plasmid

AAV plasmids for producing said rAAV particles are further disclosed.

The construction of infectious recombinant AAV (rAAV) virions has been described. See, e.g., U.S. Pat. Nos. 5,173,414 and 5,139,941; International Publication Numbers WO 92/01070 (published Jan. 23, 1992) and WO 93/03769 (published Mar. 4, 1993); Lebkowski et al. (1988) Molec. Cell. Biol. 8:3988-3996; Vincent et al. (1990) Vaccines 90 (Cold Spring Harbor Laboratory Press); Carter, B. J. (1992) Current Opinion in Biotechnology 3:533-539; Muzyczka, N. (1992) Current Topics in Microbiol, and Immunol. 158:97-129; and Kotin, R. M. (1994) Human Gene Therapy 5:793-801.

By an "AAV plasmid" is meant a plasmid derived from an adeno-associated virus serotype, including without limitation, AAV1, AAV2, AAV3, AAV4, AAV5, AAV6, AAV7, AAV8, AAV9, and AAV10, and rhesus macaque-derived serotypes including AAVrh10. AAV plasmids can have one or more of the AAV wild-type genes deleted in whole or part, preferably the rep and/or cap genes, but retain functional flanking ITR sequences. Functional ITR sequences are necessary for the rescue, replication and packaging of the AAV virion. Thus, an AAV plasmid is defined herein to include at least those sequences required in cis for replication and packaging (e.g., functional ITRs) of the virus. The ITRs need not be the wild-type nucleotide sequences, and may be altered, e.g., by the insertion, deletion or substitution of nucleotides, so long as the sequences provide for functional rescue, replication and packaging. Also by an "AAV particle" is meant the protein shell or capsid, which provides an efficient vehicle for delivery of a nucleic acid to the nucleus of target cells.

In particular, the AAV particle is derived from an adeno-associated virus selected from AAVs belonging to the AAV4, AAV5, AAVrh10 and/or AAV2 serotypes.

Preferably, the AAV particle is derived from an adeno-associated virus selected from AAVs belonging to the AAV4 or AAV5 serotypes "AAV helper functions" refer to AAV-derived coding sequences which can be expressed to provide AAV gene products that, in turn, function in trans for productive AAV replication. Thus, AAV helper functions include both of the major AAV open reading frames (ORFs), rep and cap. The Rep expression products have been shown to possess many functions, including, among others: recognition, binding and nicking of the AAV origin of DNA replication; DNA helicase activity; and modulation of transcription from AAV (or other heterologous) promoters. The Cap expression products supply necessary packaging functions. AAV helper functions are used herein to complement AAV functions in trans that are missing from AAV plasmids.

The term "AAV helper construct" refers generally to a nucleic acid molecule that includes nucleotide sequences providing AAV functions deleted from an AAV plasmid which is to be used to produce a transducing particle for delivery of a nucleotide sequence of interest. AAV helper constructs are commonly used to provide transient or stable expression of AAV rep and/or cap genes to complement missing AAV functions that are necessary for AAV replication; however, helper constructs lack AAV ITRs and can neither replicate nor package themselves. AAV helper constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. See, e.g., Samulski et al. (1989) J. Virol. 63:3822-3828; and McCarty et al. (1991) J. Virol. 65:2936-2945. A number of other plasmids have been described which encode Rep and/or Cap expression products. See, e.g., U.S. Pat. Nos. 5,139,941 and 6,376,237.

The term "transfection" is used to refer to the uptake of foreign DNA by a cell, and a cell has been "transfected" when exogenous DNA has been introduced inside the cell membrane. A number of transfection techniques are generally known in the art. See, e.g., Graham et al. (1973) Virology, 52:456, Sambrook et al. (1989) Molecular Cloning, a laboratory manual, Cold Spring Harbor Laboratories, New York, Davis et al. (1986) Basic Methods in Molecular Biology, Elsevier, and Chu et al. (1981) Gene 13:197. Such techniques can be used to introduce one or more exogenous DNA moieties into suitable host cells.

A "nucleic acid", "nucleotide sequence" or "polynucleotide sequence" refers to a DNA or RNA sequence. The term comprises sequences that include any of the known base analogues of DNA and RNA such as, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil-, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, Buracil-5-oxyacetic acid methylester, uracil-5-oxyacetic acid, pseudouracil, queosine, 2-thiocytosine, and 2,6-diaminopurine.

A "coding sequence" or a sequence which "encodes" a selected polypeptide is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. A transcription termination sequence may be located 3' to the coding sequence.

The term DNA "control sequences" refers collectively to promoter sequences, poly-adenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell. The term "promoter" is used herein in its ordinary sense to refer to a nucleotide region comprising a DNA regulatory sequence, wherein the regulatory sequence is derived from a gene which is capable of binding RNA polymerase and initiating transcription of a downstream (3-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters".

The term "heterologous" denotes sequences that are not normally joined together, and/or are not normally associated with a particular cell. Thus, a "heterologous" region of a nucleic acid construct or a plasmid is a segment of nucleic acid within or attached to another nucleic acid molecule that is not found in association with the other molecule in nature. The transgene comprising the heterologous nucleic acid can encode a number of useful products. These can include siRNA, antisense molecules, and miRNAs for example. Alternatively, transgenes can encode hormones and growth and differentiation factors.

AAV plasmids can be engineered to carry a heterologous nucleotide sequence of interest (e.g., a selected gene encoding a therapeutic protein, an antisense nucleic acid molecule, a ribozyme, a miRNA or the like) by deleting, in whole or in part, the internal portion of the AAV genome and inserting the DNA sequence of interest between the ITRs. The ITRs remain functional in such plasmids allowing replication and packaging of the rAAV containing the heterologous nucleotide sequence of interest. The heterologous nucleotide sequence is also typically linked to a promoter sequence capable of driving gene expression in the patient's target cells under the certain conditions. Termination signals, such as polyadenylation sites, can also be included in the plasmid.

The term "expression cassette" refers to a DNA nucleic acid sequence including at least one gene of interest, one open reading frame and a 3' untranslated region that, in eukaryotes, usually contains a polyadenylation site.

According to a general embodiment, an expression cassette according to the invention may thus comprise, or consist of, a DNA nucleic acid sequence having the general formula:

$$[5'ITR]\text{-}[Gene\ of\ Interest]\text{-}[PolyA]_z\text{-}[3'ITR]\text{-}$$

wherein [5'ITR] and [3'ITR] are inverted terminal repeats (ITR), wherein [Gene of Interest] is any gene coding for a protein of interest, wherein [PolyA] is a poly-adenylation signal with z being 0 or 1, and wherein each of [5'ITR], [Gene of Interest], [PolyA], and [3'ITR], can be optionally separated by one additional linker sequence.

In the sense of the invention, a "gene coding for a protein of interest" comprises at least one nucleic acid sequence coding for the protein of interest, and preferably at least one promoter.

Preferably the gene of interest is a nucleic acid coding for human PDE-6β or human RPE65.

According to one embodiment, the AAV plasmid comprises an expression cassette comprising a nucleic acid coding for human PDE-6β, of SEQ ID NO 1.

According to one alternative embodiment, the AAV plasmid comprises an expression cassette comprising a nucleic acid coding for human RPE65, of SEQ ID NO 7.

According to one particular embodiment, the AAV plasmid comprises a nucleic acid coding for human PDE6-β, of SEQ ID NO 2.

According to one embodiment, the [5'ITR] and [3'ITR] are inverted terminal repeats derived from AAV-2, which are preferably and respectively of sequences SEQ ID NO 3 and 4.

Advantageously, the AAV plasmid includes a polyadenylation site, an ITR derived from AAV2, and an expression cassette encoding human PDE6-beta.

Preferably, the expression of the human PDE6-beta gene is under the control of the promoter for Rhodopsine Kinase, preferably of sequence SEQ ID NO 5.

According to an alternative embodiment, the AAV plasmid includes a polyadenylation site, an ITR derived from AAV2, and an expression cassette encoding human RPE65.

Preferably, the expression of the human RPE65 gene is under the control of the RPE65 promoter, preferably of sequence SEQ ID NO 8.

According to one embodiment, the polyadenylation signal is derived from the Bovine Growth Hormone (bGH) and is preferably of sequence SEQ ID NO 6.

The above-mentioned embodiments may be considered individually or in combination.

According to one most preferred embodiment, the AAV plasmid comprises an expression cassette comprising a nucleic coding for PDE6β as disclosed above and as illustrated in FIG. 1A.

Figure 1B:
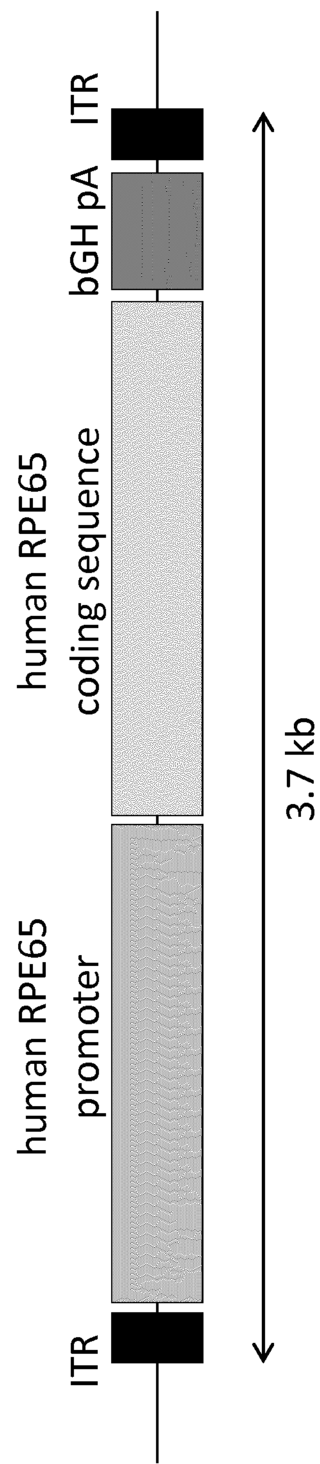
FIG. 1B: Cartography of the expression cassette of an AAV plasmid encoding human RPE65. The nucleic acid sequence coding for the human RPE65 protein is associated at its 5' end to a human RPE65 promoter and at its 3' end to a bovine growth hormone polyadenylation site (bGHpA), flanked by Inverted Terminal Repeat (ITR) sequences
Figure 2:
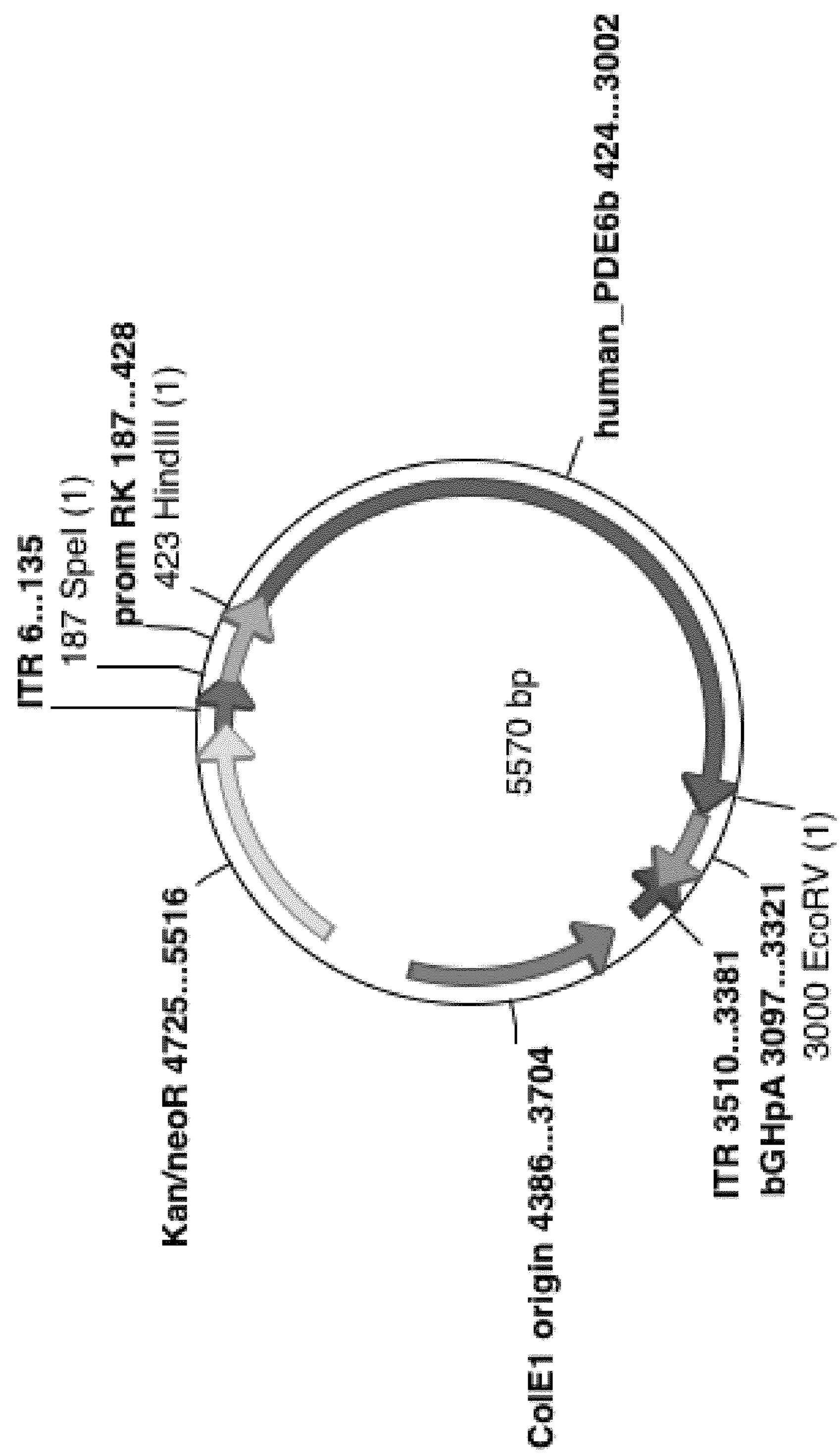
FIG. 2: Cartography of the whole AAV plasmid comprising the expression cassette encoding human PDE6β. The expression cassette is delimited by ITR sequences as defined in FIG. 1. Restriction sites are defined as EcoRV, SpeI and HindIII. The plasmid includes an additional Kanamycine (Kan/neoR) resistance marker and a Col1 origin. The directionality of sequences is indicated with arrows according to the standard nomenclature.

According to one alternative embodiment, the AAV plasmid comprises an expression cassette comprising a nucleic coding for RPE65 as disclosed above and as illustrated in FIG. 1B.

The invention further relates to a host cell which has been transfected with a AAV plasmid as defined above, and to a rAAV particle produced by said host cell.

The invention further relates to rAAV particles produced by the host cell, for use for gene therapy.

The invention further relates to rAAVs particles including an AAV plasmid as described above. In particular, the invention further relates to rAAV particles selected in a group comprising AAV1, AAV2, AAV3, AAV4, AAV5, AAV6, AAV7, AAV8, AAV 9, AAV10, and rhesus macaque-derived serotypes including AAVrh10.

In particular, rAAV particles are selected from rAAV particles belonging to the AAV4, AAV5, AAV10 (i.e. AAVrh10) and/or AAV2 serotype.

Preferably, rAAV particles are selected from rAAV particles belonging to the AAV4 and/or AAV5 serotype.

In particular, the invention relates to rAAV5 particles containing DNA comprising an expression cassette encoding human PDE6-beta as defined above.

EXAMPLES

Example 1: Two-Step Chromatography for Purifying AAV4 Particles Using a First Step of Immunoaffinity Chromatography A. Material & Methods A1. Harvest of the Cell Lysate.

Transfected cells are harvested at 96+/−5 hours post transfection by rapping the CellStacks 10 (CS10) on all sides. The entire suspension is transferred in a BioProcess Container (BPC). A major part of the viral particle is released in the supernatant.

At this step the major part of the viral vector is already released in the supernatant but a 0.5% (v/v) Triton X-100 treatment (1 hour, stirring, at room temperature) is necessary to optimize the extraction of AAV4 from the cells, to contribute to detach the particles from impurities, and finally to optimize the recovery of AAV4 in the supernatant and to optimize the next step of depth filtration.

A2. Clarification of the Cell Lysate.

The suspension obtained after the action of Triton X-100 is filtered through a Millipore depth filter Polysep II 1/0.2 μm to discard the cell debris. At the end of the filtration step, the filtration unit is emptied by pushing with air. This is the clarified lysate.

During this step a great part of DNA and soluble proteins are discarded as well.

A3. Chromatographic Immuno-Affinity Purification Step

This step is performed with an Akta Pilot (GE Healthcare) controlled by a Unicorn software. The clarified lysate is injected at 150 cm/h linear flow rate through an AVB column 185 mL of packed matrice equilibrated with DPBS supplemented with Calcium and Magnesium. During this step the AAV binds specifically to the column. Impurities do not bind to the column and are discarded in the flowthrough. To wash the unspecific bound material, the column is then rinsed with DPBS.

AAV is eluted with a PBS pH 2.0 buffer. Eluted fractions are simultaneously neutralized with 10% of Buffer Tris 1M, $MgCl_2$ 20 mM, CaCl 10 mM, pH 8.5.

Eluted fractions neutralized with Tris buffer are frozen at <−70° C., or even <−80° C. until titration of AAV by QPCR to detect the amount of AAV in each fraction.

A4. 1$^{st}$ Alternative: CsCl Gradient after Immuno-Affinity Purification Step.

Fractions eluted from the AVB column and containing the AAV are pooled. To precipitate AAV and to obtain a suitable volume for gradient, PEG 8 000 is added to obtain 8% final. After an overnight precipitation with PEG 8% (w/v), the AAV containing suspension is centrifuged at 4 000 rpm for 1 hour at 4° C.

The AAV-containing pellet is resuspended in 12 mL of 1,376 g/cm3 density CsCl, transferred to an UltraClear tube for SW41 rotor. The gradient is centrifuged at 38,000 rpm for 48 hours at 15° C. to separate full particles from "empty" one. The enriched-full particles band is collected with a 5 or 10 mL syringe. The viral suspension is then subjected to Tangential Flow Filtration (TFF).

A5. 2$^{nd}$ Alternative: CIMmultus Anion-Exchange Chromatography after after Immuno-Affinity Purification Step.

This step is realised with an Akta Pilot (GE Healthcare) controlled by a Unicorn software.

Fractions eluted from the AVB column and containing the AAV are pooled and submitted to a TFF step for diafiltration. The goal of this TFF step is to change the buffer of neutralized eluted fractions from AVB to be able to bind AAV to the CIMmultus QA column.

The diafiltered AAV is then injected through a Monolith CIMmultus QA column equilibrated with buffer 1: Tris 20 mM, NaCl 10 mM, MgCl2 2 mM, CaCl2 1 mM, pH 8.5 to promote the binding of AAV to the column.

At the end of the injection of the AAV containing suspension, the column is washed with buffer 1 to discard everything that could be bound unspecifically.

The elution step is a NaCl salt gradient with a very shallow slope which is the result of mixing buffer 1 (Tris 20 mM, NaCl 10 mM, MgCl2 2 mM, CaCl2 1 mM, pH 8.5) with buffer 2 (Tris 20 mM, NaCl 1 M, MgCl2 2 mM, CaCl2 1 mM, pH 8.5). The slow increase of salt allows to elute gradually AAV and to separate sub populations as full and empty particles if sub populations are present.

Eluted fractions are collected in polypropylene bottles and stored at <−70° C., or even <−80° C., until the TFF.

A6. Tangential Flow Filtration (TFF).

Selected fractions are pooled (around 1 L in volume). TFF is done using a mPES hollow fiber with a cut off of 30 KDa. AAV is diafiltered and concentrated against Saline Ocular Solution (SSO).

The pooled fractions are first slightly concentrated, diafiltered against 10 volumes of buffer and finally concentrated to reach the expected concentration. TFF allows to discard the remaining small size impurities as well as to formulate the viral vector in the right buffer for injection and to concentrate to the right level. The filtered purified and concentrated viral vector is stored at <−70° C., or even <−80° C., until titration.

A7. Sterile Filtration.

AAV is diluted with SSO (Saline Ocular Solution) to obtain the precise concentration necessary for the injection to patients and sterile filtered with a 0.2 μm PES filter before to be aliquoted in final container according to the expected volume. Doses are stored at <−80° C. until injection.

A8. Vector Genome Concentration by qPCR (vg/mL)

This method consists in the determination of genome-containing particles by quantitative PCR (qPCR) targeting the expression cassette of the transgene (the transgene, the poly(A), the ITR or the promoter). The rAAV samples are first digested with DNase in order to eliminate non-encapsidated DNA. Afterwards, a Proteinase K treatment degrades AAV capsids and releases the viral DNA for the subsequent qPCR quantification.

The vector plasmid containing the targeted amplicon is used to generate the standard curve for the qPCR. This plasmid is linearized by restriction endonuclease digestion, aliquoted and stored at ≤−18° C. to ensure stability and reproducibility of the standard curve in each assay.

The calculation of 1$^{e}$10 copies of amplicon is based on the following formula:

Quantity of DNA (g)=(660×plasmid size (bp)×1$^{e}$10 copies)/(6.02×10$^{e}$23)

The relative quantity of vector genome DNA is assigned by extrapolation of copy number per reaction from the standard curve containing a known amount of amplicon DNA.

The results are reported in vector genome per mL.

A9. Infectious Particles Concentration by ICA (ip/mL)

The Infectious Center Assay (ICA) allows the quantification of infectious particles in a rAAV lot. This assay involves the infection of a permissive cell line stably carrying the AAV2 rep and cap sequences (HeLaRC32, ATCC CRL-2972) with increasing serial dilutions of the rAAV vector and with wild-type Adenovirus (type 5). Thus, infectious rAAV particles entering into the cells will be able to replicate. The replication events are then detected by chemiluminescence and quantified following hybridization with a transgene specific probe (Salvetti et al., Hum Gene Ther, 1998).

Twenty-six hours post-infection, the cells are harvested, lysed and blotted on a nylon membrane. An hybridization is performed with a specific transgene probe labeled with fluorescein. The signal is then amplified with an anti-fluorescein antibody coupled with Alkaline Phosphatase and detected by chemiluminescence.

Finally, the replication events are quantified by dot counting after revelation on a radiographic film.

A10. Vector Capsid Purity and Identity by SDS-PAGE and Coomassie Blue Staining.

The SDS-PAGE method is an electrophoresis in a polyacrylamide gel in denaturing conditions that separates the proteins and the other components of the sample depending on their molecular weight and their charges.

After electrophoresis, the gel is stained with Coomassie blue (Imperial Protein Stain) in order to quantify only the proteins in the samples. The protein identity of the rAAV is confirmed by the presence of the three capsids proteins of AAV called VP1, VP2 and VP3 relating to their molecular weight (87, 72 and 62 KDa). The protein purity of rAAV is calculated as a relative amount of capsid proteins compared to the total amount of proteins present in the sample.

The electrophoresis gel is analyzed after Coomassie blue staining by a luminescent image analyzer with a CCD camera. Each band of protein is detected as a peak and the signal is integrated by the analyzer. The area of each peak is then calculated; a 100% pure product contains only the three VP1, VP2 and VP3 protein bands.

A11. Vector Particles Quantification by SDS-PAGE and Silver Staining

The silver staining, based on the methodology of Heukeshoven and Dernick (Heukeshoven and Dernick Electrophoresis, 1985), allows the detection of proteins and nucleic acids separated by polyacrylamide gel electrophoresis.

The sample is loaded on the same gel as the rAAV used for the standard curve. The standard curve is generated using a referent rAAV lot, produced and characterized in the same way as the rAAV8RSM (Ayuso et al, Hum Gene Ther. 2014), and containing 100% full particles.

After electrophoresis, the gel is analyzed using an image analyzer with a CCD camera, and the signal of the band corresponding to VP3 is integrated for each lane. The quantity of total capsids present in the sample is extrapolated from the standard curve, and reported in particles per mL.

The ratio full/total particles is based on the following calculation: Titer in vector genome per mL/titer in particles per mL.

For reference: Simplified method for silver staining of proteins in polyacrylamide gels and the mechanism of silver staining. (Electrophoresis 6 (1985) 103-112, Heukeshoven, J. and Dernick, R.) & Manufacturing and Characterization of a recombinant associated virus type 8 reference standard material, Ayuso et al, (Hum Gene Ther. 2014 Oct. 2).

A12. Residual Host Cell DNA by qPCR (Albumin and E1A from HEK 293 Cells)

The residual Human Host Cell DNA is determined using a real-time quantitative PCR method targeting the human albumin or the adenovirus type 5 E1A genes.

A plasmid containing the specific amplicons (albumin and E1A) is used to generate the standard curve for the qPCR. This plasmid is linearized by restriction endonuclease digestion, filled and stored at ≤−18° C. to ensure stability and reproducibility of the standard curve in each assay. The calculation of $1^e10$ copies of albumin gene sequence is based on the following calculation:

$$\text{Quantity of DNA (g)}=(660\times\text{plasmid size (bp)}\times 1e10\ \text{copies})/6.02\times 10e23.$$

The relative quantity of albumin or E1A amplicon DNA is assigned by extrapolation of copy number per reaction from the standard curve containing a known amount of albumin or E1A amplicon DNA.

A second standard curve is performed with genomic DNA from HEK293 cell line, from 50 μg to 5 ng per well. This standard curve indicates the correlation between the amount of albumin or E1A copy and the corresponding amount in ng of HEK293 DNA.

B. Results

Figure 3A:
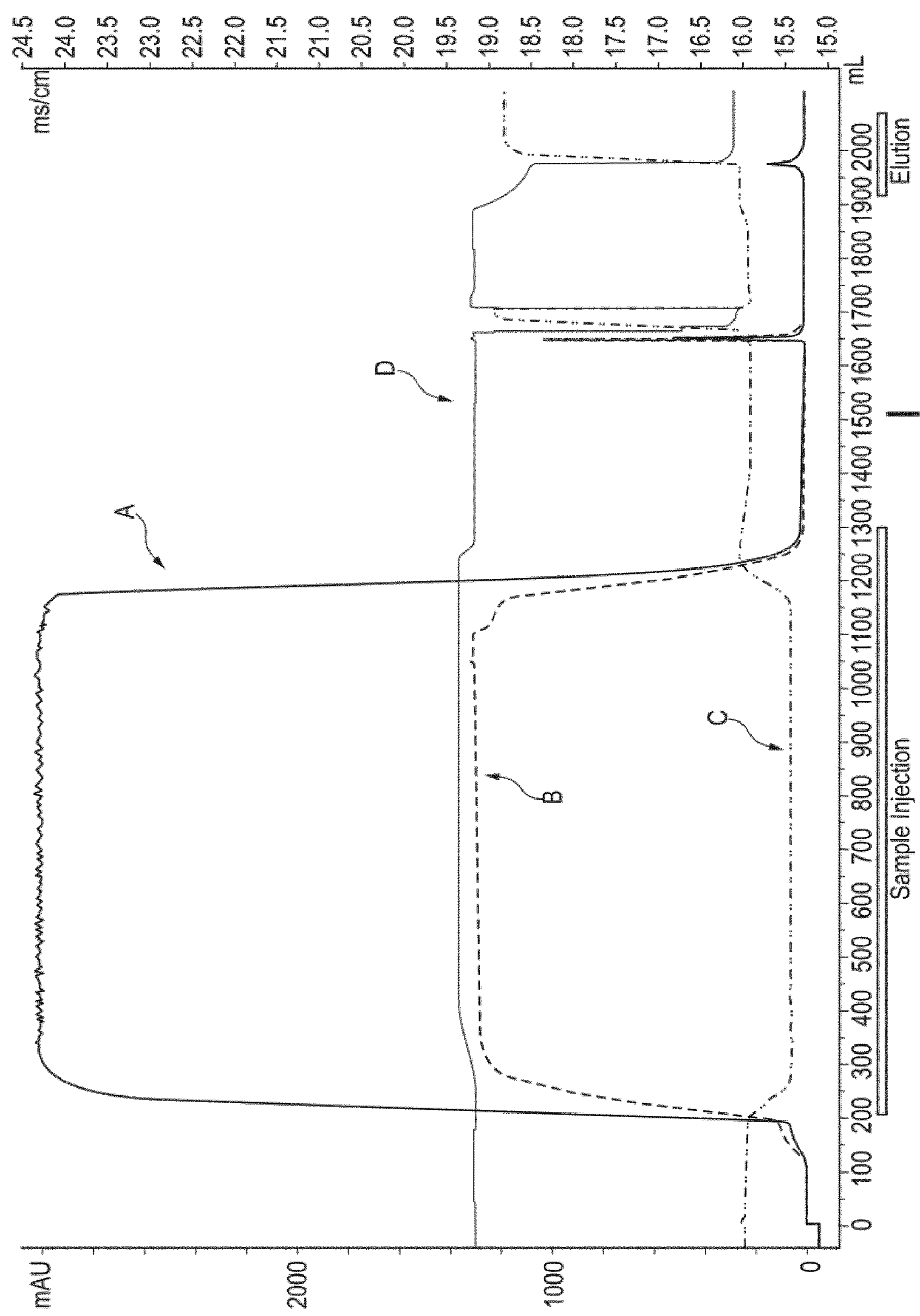
FIG. 3A: Chromatogram of the complete AVB column step Curves represent Absorbance (left axis in mAU) at 280 nm (A line) and 260 nm (B line). Line C represents the conductivity in mS/cm (right axis). Line D represents pH. Empty squares show the sample injection and elution steps.
Figure 3B:
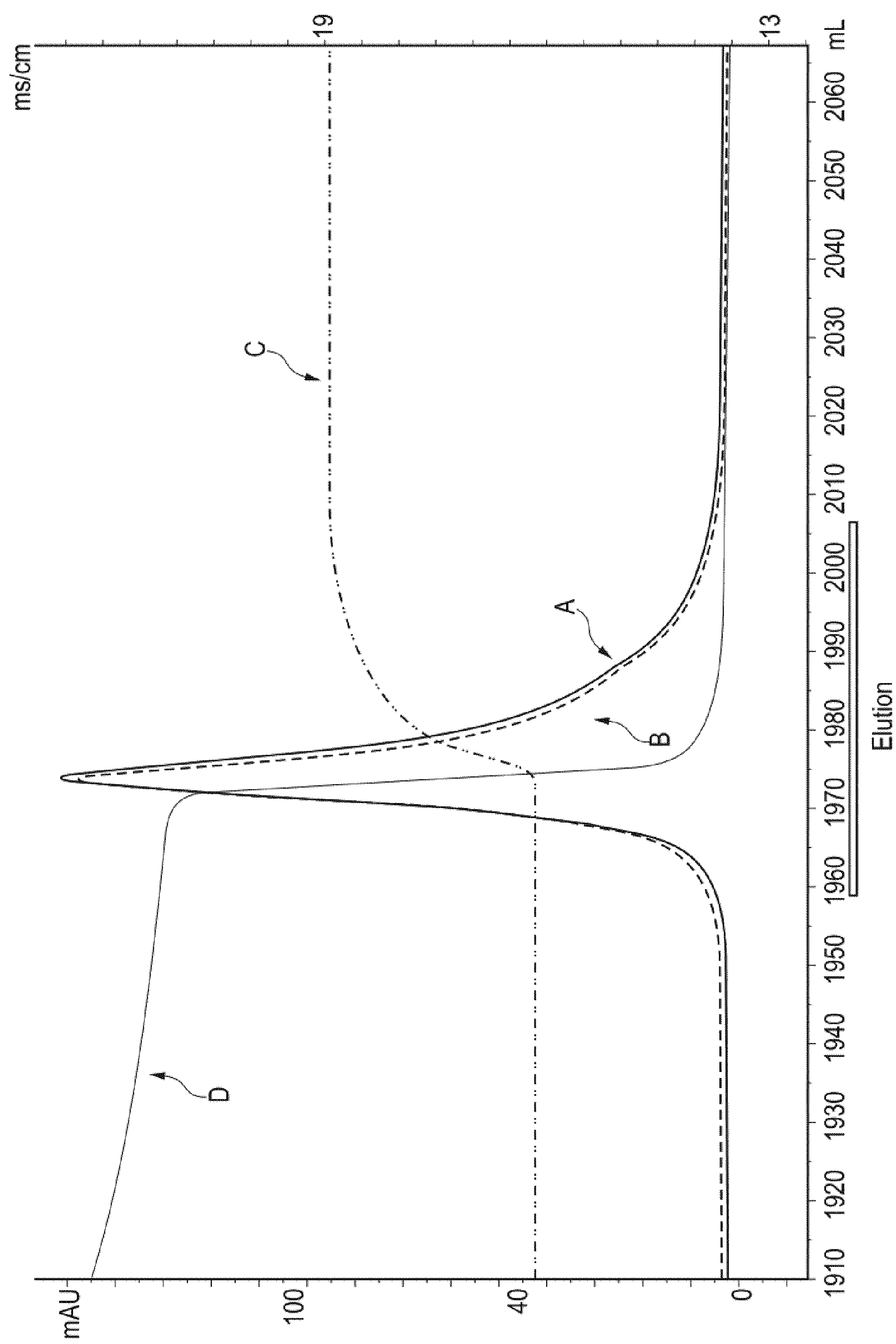
FIG. 3B: Zoom peak of the eluted AAV from the AVB column step Curves represent Absorbance (left axis in mAU) at 280 nm (A line) and 260 nm (B line). Line C represents the conductivity in mS/cm (right axis). Line D represents pH. Empty square shows where the AAVs-containing fractions are eluted.

FIGS. 3A and 3B illustrate the elution profile of a clarified supernatant containing AAV4 particles, from a step of Immunoaffinity chromatography (see FIG. 3A) on an AVB column. Close-up of the elution profile peak is further disclosed in FIG. 3B.

The purification method is achieved at a 1 L scale Titration of the vector genome at each step and characterization of the final product are established according to the above mentioned procols and summarized in the following tables:

TABLE 1

| titration of the vector genome from a 1L scale purification | |
|---|---|
| Harvest | $1.1.\ 10^{14}$ |
| Depth filtration | $9.2.\ 10^{13}$ |
| AVB column | $8.7.\ 10^{13}$ |
| Tangential Flow Filtration | $7.2.\ 10^{13}$ |
| Total Yield | 65% |

TABLE 2

| characterization of the final product | |
|---|---|
| Titer (vg/mL) | $3.8\ 10^{12}$ |
| resDNA (Alb) ng/dose* | 1.2 |
| resDNA (E1A) ng/dose* | 15 |
| Purity (Proteins) | 100% |

*where a dose is $1\ 10^{12}$ vector genome (vg).

Conclusion: this protocol is efficient for purifying clinical-grade AAV4 preparation from clarified supernatant at a 1 L scale, and in very good yields. Advantageously, the AVB column immunochromatography step only impacts moderately the amount of the vector genome.

Example 2: Two-Step Chromatography for Purifying AAV4 Particles Using a First Step of Immunoaffinity Chromatography, Followed by a Second Step of Anion-Exchange Chromatography (Alternative Protocol)

A. Material & Methods

The Material & Methods section of Example 1 is also applicable to Example 2 apart from:

A3. Chromatographic Immuno-Affinity Purification Step (Alternative Protocol)

This step is performed with an Akta Pilot (GE Healthcare) controlled by a Unicorn software. The clarified lysate is injected at 150 cm/h linear flow rate through an AVB column (185 mL of packed matrix) equilibrated with PBS. During this step the AAV binds specifically to the column. Impurities do not bind to the column and are discarded in the flowthrough. To wash the unspecific bound material, the column is then rinsed with PBS.

AAV is eluted with a PBS pH 2.0 buffer. Eluted fractions are simultaneously neutralized with 10% of Buffer Tris 1M, $MgCl_2$ 20 mM, CaCl 10 mM, pH 8.

Eluted fractions neutralized with Tris buffer are supplemented with 0.001% of Pluronic F68 and frozen at <−70° C., or even <−80° C., until titration of AAV by QPCR to detect the amount of AAV in each fraction.

A4. 1st Alternative: CsCl Gradient after Immuno-Affinity Purification Step (Alternative Protocol)

Fractions eluted from the AVB column and containing the AAV are pooled. To concentrate AAV and to obtain a suitable volume for gradient, the pool of AAV fractions is submitted to a Tangential Flow Filtration against Saline Ocular Solution with 0.001% of Pluronic F68.

The diafiltered AAV is resuspended in 12 mL of 1,376 g/cm3 density CsCl, transferred to an UltraClear tube for SW41 rotor. The gradient is centrifuged at 38,000 rpm for 48 hours at 15° C. to separate full particles from "empty" one. The enriched-full particles band is collected with a 5 or 10 mL syringe. The viral suspension is then subjected to Tangential Flow Filtration (TFF).

A5. 2nd Alternative: CIMmultus Anion-Exchange Chromatography after Immuno-affinity Purification Step (Alternative Protocol).

This step is realised with an Akta Pilot (GE Healthcare) controlled by a Unicorn software.

Fractions eluted from the AVB column and containing the AAV are pooled and submitted to a TFF step for diafiltration. The goal of this TFF step is to change the buffer of neutralized eluted fractions from AVB to be able to bind AAV to the CIMmultus QA column.

All the buffers used during the IEX chromatography step contain 0.001% of Pluronic F68.

The diafiltered AAV is injected through a Monolith CIMmultus QA column equilibrated with buffer 1: Tris 20 mM, NaCl 10 mM, MgCl2 2 mM, CaCl2 1 mM, pH 9 to promote the binding of AAV to the column.

At the end of the injection of the AAV containing suspension, the column is washed with buffer 1 to discard everything that could be bound unspecifically.

The elution step is a NaCl salt gradient with a very shallow slope which is the result of mixing buffer 1 (Tris 20 mM, NaCl 10 mM, MgCl2 2 mM, CaCl2 1 mM, pH 8) with buffer 2 (Tris 20 mM, NaCl 500 mM, MgCl2 2 mM, CaCl2 1 mM, pH 8). The slow increase of salt allows to elute gradually AAV and to separate sub populations as full and empty particles if sub populations are present.

Eluted fractions are collected in polypropylene bottles and stored at <−70° C., or even <−80° C. until the TFF.

A6. Tangential Flow Filtration (TFF) (Alternative Protocol).

Selected fractions are pooled (around 0.5 L in volume). TFF is done using a mPES hollow fiber with a cut off of 100 KDa. AAV is diafiltered and concentrated against Saline Ocular Solution (SSO) containing Pluronic F68 0.001%.

The pooled fractions are first slightly concentrated, diafiltered against 10 volumes of buffer and finally concentrated to reach the expected concentration. TFF allows to discard the remaining small size impurities as well as to formulate the viral vector in the right buffer for injection and to concentrate to the right level. The filtered purified and concentrated viral vector is stored at <−70° C., or even <−80° C., until titration.

A7. Sterile Filtration (Alternative Protocol).

AAV is diluted with SOS (Saline Ocular Solution) containing Pluronic F68 to obtain the precise concentration necessary for the injection and sterile filtered with a 0.2 μm PES filter before to be aliquoted in final container according to the expected volume. Doses are stored at <−70° C., or even <−80° C. until injection.

B. Results

B1 AAV4 Results at 1 L Scale

The purification method is achieved at a 1 L scale. The second step is either an IEX chromatography step or a Cscl gradient, as indicated in Table 3. Titration of the vector genome at each step is summarized in the following table:

TABLE 3 titration of the vector genome from a 1L scale purification (Alternative protocol)

| | Affinity + CsCl gradient | Affinity + IEX |
|---|---|---|
| Harvest | $1.1\ 10^{14}$ | $7.0\ 10^{13}$ |
| Depth filtration | $9.8\ 10^{13}$ | $6.9\ 10^{13}$ |
| AVB column | $1.3\ 10^{14}$ | $6.9\ 10^{13}$ |
| Tangential Flow Filtration 1 | $7.8\ 10^{13}$ | $4.8\ 10^{13}$ |
| 2nd step (CsCl or IEX) | $5.3\ 10^{13}$ | $3.4\ 10^{13}$ |
| Tangential Flow Filtration 2 | $4.4\ 10^{13}$ | $2.7\ 10^{13}$ |
| Final Product (0.2 μm filtered) | $3.9\ 10^{13}$ | $3.0\ 10^{13}$ |
| Total Yield | 35% | 43% |
| Purity | >90% | >90% |

B2 AAV4 Results at 3 L Scale

This is an example of a 3 L scale, where AAV4 is purified with the process described above comprising a Triton X-100 extraction, a depth filtration, an affinity chromatography step, a TFF, a IEX chromatography step, a TFF and a 0.2 μm sterile filtration.

In the Table 4 are summarized the results of each step, by titration of the vector genome.

The elution profile is obtained from the IEX chromatography step. Each fraction is analyzed on a silver stained SDS Polyacrylamide gel. All the fractions were loaded at the same vector genome amount. The signal of capsid proteins, more important in the first fractions, and the ratio of absorbance curves at 280 and 254 nm, show that the first fractions eluted are mostly contaminated by empty capsids.

The selected fractions mostly comprise full capsids.

The intensity of capsid proteins of each fraction was compared to a reference AAV4 preparation obtained by purification on a two-CsCl gradient process and containing >90% of full particles.

TABLE 4 titration of the vector genome from a 3L scale purification

| | Affinity + IEX |
|---|---|
| Harvest | $2.9\ 10^{14}$ |
| Depth filtration | $4.3\ 10^{14}$ |
| Affinity AVB column | $5.9\ 10^{14}$ |
| Tangential Flow Filtration 1 | $3.7\ 10^{14}$ |
| IEX CIM QA column | $1.9\ 10^{14}$ |
| Tangential Flow Filtration 2 | $1.6\ 10^{14}$ |
| Final Product (0.2 μm filtered) | $1.3\ 10^{14}$ |
| Total Yield | 45% |

TABLE 5 characterization of the final product

| | Affinity + IEX |
|---|---|
| Titer (vg/mL) | $3.4\ 10^{12}$ |
| Infectious Titer (pi/mL) | $3.7\ 10^{6}$ |
| Ratio vg/pi | $9.3\ 10^{5}$ |
| Purity (Proteins) | >99% |
| resDNA (Alb) ng/dose* | <0.25 |

TABLE 5-continued

| characterization of the final product | |
|---|---|
| | Affinity + IEX |
| resDNA (E1A) ng/dose* | 21.4 |

*where a dose is 1*10[12] vector genome (vg)

It is to note that the ratio vg/pi is very high due to the poor permissivity of HeLa cells for AAV4. Nevertheless this ratio is comparable to the ratio of the AAV4 reference preparation.

Conclusion: this protocol is efficient for purifying clinical-grade AAV4 preparation from clarified supernatant at a 3 L scale, and in very good yields. Advantageously, the IEX column chromatography step impacts the amount of the full particles.

Example 3: Two-Step Chromatography for Purifying AAVrh10 Particles Using a First Step of Immunoaffinity Chromatography, Followed by a Second Step of Cscl Gradient or Anion-Exchange Chromatography (Alternative Protocol)

A. Material & Methods

The Material & Methods section of Example 1 is also applicable to Example 3 apart from:

A1. Harvest of the Cell Lysate (Alternative Protocol)

Insect Sf9 cells infected with baculoviruses in a 2 L bioreactor are collected at 96+/−5 hours post infection. The entire suspension is treated with Triton X-100 (0.5% v/v final, 27° C., during 2.5 hours). A major part of the viral particle is released in the supernatant.

A3. Chromatographic Immuno-Affinity Purification Step (Alternative Protocol)

This step is performed with an Akta Pilot (GE Healthcare) controlled by a Unicorn software. The clarified cell lysate is injected at 60 cm/h linear flow rate through an AVB column (185 mL of packed matrix) equilibrated with DPBS supplemented with Calcium and Magnesium. During this step the AAV binds specifically to the column. Impurities do not bind to the column and are discarded in the flowthrough. To wash the unspecific bound material, the column is then rinsed with DPBS.

AAV is eluted with a citric acid buffer 50 mM containing 300 mM NaCl, pH 3.4. Eluted fractions are simultaneously neutralized with 10% of Buffer Tris 1M, $MgCl_2$ 20 mM, CaCl 10 mM, pH 8.5.

A4. 1$^{st}$ Alternative: CsCl Gradient after Immuno-Affinity Purification Step (Alternative Protocol)

Fractions eluted from the AVB column and containing the peak of AAV (detected by the measure of absorbance at 280 and 254 nm) are pooled. To concentrate AAV and to obtain a suitable volume for gradient, the pool of AAV fractions is submitted to a PEG 8 000 precipitation overnight at 4° C. followed by a centrifugation at 4 000 rpm during 1 hour at 4° C. The pellet is resuspended in 12 mL of 1,376 g/cm3 density CsCl, transferred to an UltraClear tube for SW41 rotor. The gradient is centrifuged at 38,000 rpm for 48 hours at 15° C. to separate full particles from “empty” one. The enriched-full particles band is collected with a 5 or 10 mL syringe. The viral suspension is then subjected to a dialysis against DPBS with Calcium and Magnesium. The dialysed viral suspension is supplemented with 0.001% of Pluronic F68 and frozen at <−80° C.

A5. 2$^{nd}$ Alternative: POROS HQ Anion-Exchange Chromatography after Immuno-Affinity Purification Step (Alternative Protocol).

This step is realised with an Akta Explorer (GE Healthcare) controlled by a Unicorn software.

Fractions eluted from the AVB column and containing the AAV are pooled, supplemented with 0.001% of Pluronic F68 and stored at 4° C. overnight. The day after, the AAV pool is submitted to a TFF step for diafiltration. The goal of this TFF step is to change the buffer of neutralized eluted fractions from AVB to be able to bind AAV to the POROS HQ column.

The diafiltered AAV is injected through a POROS HQ column equilibrated with buffer 1: Tris 20 mM, MgCl2 2 mM, CaCl2 1 mM, pH 8.5 to promote the binding of AAV to the column.

At the end of the injection of the AAV containing suspension, the column is washed with buffer 1 to discard everything that could be bound unspecifically.

The elution step is a Na Citrate salt gradient with a very shallow slope which is the result of mixing buffer 2 (Tris 10 mM, Na Citrate 10 mM MgCl2 2 mM, CaCl2 1 mM, pH 8 with 0.001% Pluronic F68) with buffer 3 (Tris 10 mM, Na Citrate 500 mM, MgCl2 2 mM, CaCl2 1 mM, pH 8, with 0.001% Pluronic F68). The slow increase of salt (gradient to obtain 70% of buffer 3 in 40 column volumes) allows to elute gradually AAV and to separate sub populations as full and empty particles if sub populations are present.

Eluted fractions are collected in polypropylene tubes and stored at <−80° C. until the TFF.

A6. Tangential Flow Filtration (TFF) (Alternative Protocol).

Selected fractions are pooled. TFF is done using a mPES hollow fiber with a cut off of 100 KDa. AAV is diafiltered and concentrated against DPBS with Calcium and Magnesium containing Pluronic F68 0.001%.

The pooled fractions are first slightly concentrated, diafiltered against 10 volumes of buffer and finally concentrated to reach the expected concentration. The filtered purified and concentrated viral vector is stored at <−80° C. until titration.

B. Results

B1 AAVrh10 Results at 1 L Scale

The purification method is achieved at a 1 L scale. The second step is either a CsCl gradient or an IEX chromatography step, as indicated in Table 6. Titration of the vector genome at each step is summarized in the following table:

TABLE 6

| titration of the vector genome equivalent to 1L scale purification (Alternative protocol) | | |
|---|---|---|
| | Affinity + CsCl gradient | Affinity + IEX |
| Clarified cell lysate | 5.1 $10^{13}$ | 6.2 $10^{13}$ |
| AVB column | 2.9 $10^{13}$ | 2.5 $10^{13}$ |
| Tangential Flow Filtration 1 | Non Applicable | 1.6 $10^{13}$ |
| 2$^{nd}$ step (CsCl or IEX) | 3.1 $10^{13}$ | 1.5 $10^{13}$ |
| Formulated Purified Product | 2.5 $10^{13}$ | 1.5 $10^{13}$ |
| Total Yield | 49% | 24% |

Example 4: Two-Step Chromatography for Purifying AAV2 Particles Using a First Step of Immunoaffinity Chromatography, Followed by a Second Step of Cscl Gradient (Alternative Protocol)

A. Material & Methods

The Material & Methods section of Example 1 is also applicable to Example 4 apart from:

A1. Harvest of the Cell Lysate (Alternative Protocol)

Insect Sf9 cells infected with baculoviruses in a 2 L bioreactor are collected at 96+/−5 hours post infection. The entire suspension is treated with Triton X-100 (0.5% v/v final, 27° C., during 2.5 hours). An additional step of nuclease digestion is realised by adding Benzonase 5 U/mL during 2 additional hours at 37° C.

A3. Chromatographic Immuno-Affinity Purification Step (Alternative Protocol)

This step is performed with an Akta Pilot (GE Healthcare) controlled by a Unicorn software. The clarified lysate is injected at 115 cm/h linear flow rate through an AVB column (185 mL of packed matrix) equilibrated with DPBS supplemented with Calcium and Magnesium. During this step the AAV binds specifically to the column. Impurities do not bind to the column and are discarded in the flowthrough. To wash the unspecific bound material, the column is then rinsed with DPBS.

AAV is eluted with a citric acid buffer 50 mM containing 300 mM NaCl, pH 3.4. Eluted fractions are simultaneously neutralized with 10% of Buffer Tris 1M, $MgCl_2$ 20 mM, CaCl 10 mM, pH 8.5.

A4. 1$^{st}$ Alternative: CsCl Gradient after Immuno-Affinity Purification Step (Alternative Protocol)

Fractions eluted from the AVB column and containing the peak of AAV (detected by the measure of absorbance at 280 and 254 nm) are pooled. To concentrate AAV and to obtain a suitable volume for gradient, the pool of AAV fractions is submitted to a PEG 8 000 precipitation overnight at 4° C. followed by a centrifugation at 4 000 rpm during 1 hour at 4° C. The pellet is resuspended in 12 mL of 1,376 g/cm3 density CsCl, transferred to an UltraClear tube for SW41 rotor. The gradient is centrifuged at 38,000 rpm for 48 hours at 15° C. to separate full particles from "empty" one. The enriched-full particles band is collected with a 5 or 10 mL syringe. The viral suspension is then subjected to a dialysis against DPBS with Calcium and Magnesium. The dialysed viral suspension is supplemented with 0.001% of Pluronic F68 and frozen at <−80° C.

A7. Sterile Filtration.

AAV is filtered with a 0.2 μm PES filter before to be aliquoted in final container according to the expected volume. Doses are stored at <−80° C.

B. Results

B1 AAV2 Results at 1 L Scale

The purification method is achieved at a 1 L scale. The second step is a Cscl gradient, as indicated in Table 7. Titration of the vector genome at each step is summarized in the following table:

TABLE 7 titration of the vector genome equivalent to 1L scale purification (Alternative protocol)

| | Affinity + CsCl gradient |
|---|---|
| Clarified cell lysate | 3.2 $10^{13}$ |
| AVB column | 1.7 $10^{13}$ |
| 2$^{nd}$ step (CsCl or IEX) | 9.2 $10^{12}$ |
| Formulated Purified Product | 6.6 $10^{12}$ |
| Total Yield | 21% |

Example 5: Comparison Between the Method of the Invention and a Method for Purifying rAAV Particles Comprising Cation- and Anion-Exchange Chromatographies A. Material & Methods Description of the Method Comprising Cation- and Anion-Exchange Chromatographies Transfected cells were harvested between 48 and 72 hours post transfection by rapping the CellStacks 5 (CS5) on all sides. The entire suspension of AAV4 was lysed by homogenization in a high pressure homogenizer (Emulsiflex C55, Avestin) at 900+/−50 bars. The pressure drop in this system leads to the disrupture of cells, allowing the extraction of AAV particles in the supernatant and the reduction of cell debris size.

The homogenized cell lysate is depth filtered through a Millistack COHC unit (Merck Millipore) and a PES 0.5/0.2 μm filter to discard the cell debris.

The clarified cell lysate was pre-purified and concentrated with a Mustang Q (Pall Life Science) step: this anionic exchange membrane allows to bind AAV to the membrane at high flow rate and then to elute selectively AAV with NaCl discarding around 80% DNA and 50% protein impurities. The low volume of elution allows to concentrate 100 times the AAV product.

Pre-purified AAV was stored at <−80° C.

Pre-purified AAV from Mustang Q was further purified through a Capto MMC column (GE Healthcare), which is a multimodal chromatography matrix involving cationic exchange and hydrophobic interactions properties. AAV4 was eluted with a buffer containing 600 mM NH4Cl and stored at <−80° C.

The eluted AAV from Capto MMC was diluted to adjust the conductivity and pH parameters to bind on the last chromatography support, a Capto Q column (GE Healthcare). This anion exchange step is a polishing step where AAV was eluted with a Tris buffer containing 180 mM NaCl.

Eluted AAV from Capto Q was diafiltered with a 100 KDa hollow fiber (GE Healthcare) allowing to formulate and to concentrate the AAV. The diafiltered AAV was stored at <−80° C. and finally 0.2 μm sterile filtered.

Description of the Method of the Invention rAAV4 particles were purified according to the method of the invention as described in Example 1.

B. Results

Total Yield obtained with the method comprising cation- and anion-exchange chromatography is about 1-2%, whereas total Yield obtained with the method of the invention is at least 20%.

| SEQUENCE LISTING | |
|---|---|
| SEQ ID No 1 | Expression cassette encoding human PDE6β |
| SEQ ID No 2 | Nucleic acid coding for human PDE6-β |

-continued

SEQUENCE LISTING

| | |
|---|---|
| SEQ ID No 3 | [5'ITR] inverted terminal repeat derived from AAV-2 |
| SEQ ID No 4 | [3'ITR] inverted terminal repeat derived from AAV-2 |
| SEQ ID No 5 | Promoter for Rhodopsine Kinase |
| SEQ ID No 6 | [PolyA] signal derived from the Bovine Growth Hormone (bGH) |
| SEQ ID No 7 | Expression cassette of human RPE65 |
| SEQ ID No 8 | Human RPE65 gene promoter |
| SEQ ID No 9 | Nucleic acid coding for human RPE65 |

-continued

SEQUENCE LISTING

| | |
|---|---|
| SEQ ID No 10 | AAV-4 VP1 coding sequence (2205 nt) |
| SEQ ID No 11 | AAV-4 VP2 coding sequence (409-2205 of VP1) |
| SEQ ID No 12 | AAV-4 VP3 coding sequence (589-2205 of VP1) |
| SEQ ID No 13 | AAV-5 VP1 coding sequence (2175 nt) |
| SEQ ID No 14 | AAV-5 VP2 coding sequence (409-2175 of VP1) |
| SEQ ID No 15 | AAV-5 VP3 coding sequence (577-2175 of VP1) |

The invention claimed is:

1. A method for obtaining purified recombinant Adeno-Associated Virus (rAAV) particles, comprising the steps of:

a) treating a starting material previously obtained from cells producing rAAV particles with a detergent, said starting material comprising a cell lysate and/or a culture supernatant;

b) performing a depth filtration of said a starting material using a depth filter membrane comprising borosilicate glass microfibers and mixed esters of cellulose, whereby a rAAV-containing clarified composition is provided;

c) submitting the rAAV-containing clarified composition to an immunoaffinity purification step and eluting the rAAV particles at acidic pH, whereby a first rAAV-enriched composition is provided;

d) neutralizing the acidic pH of said first rAAV-enriched composition of step c) to neutral or basic pH;

e) submitting the first rAAV-enriched composition of step d) at least once to:

e1) a step of anion-exchange chromatography on a chromatographic support, wherein elution is performed by using a salt gradient and wherein the rAAV-containing fraction is collected, whereby a second rAAV-enriched composition is provided; or e2) a step of density gradient centrifugation, wherein the rAAV-containing fraction is collected, whereby a second rAAV-enriched composition is provided;

f) submitting the second rAAV-enriched composition to a step of tangential flow filtration, whereby purified recombinant Adeno-Associated Virus (rAAV) particles are provided, wherein the method does not comprise an apatite chromatography step or a cation-exchange chromatography step, and wherein the rAAV particles belong to an AAV serotype selected from the group consisting of AAV4, AAVrh10, AAV2, AAV8, and AAV9.

2. The method according to claim 1, wherein step c) is performed by using a chromatography support onto which antibodies or fragments thereof directed to said rAAV particles are immobilized.

3. The method according to claim 2, wherein said antibodies or fragments thereof are monoclonal.

4. The method according to claim 2, wherein said antibodies or fragments thereof are camelid antibodies or fragments thereof.

5. The method according to claim 1, wherein at step e1), the chromatographic support is a monolithic chromatographic support.

6. The method according to claim 1, wherein step f) is performed by using a filter membrane having a molecular weight cut-off value ranging from 20 kDa to 150 kDa.

7. The method according to claim 1, wherein the rAAV particles belong to the AAV serotype AAV4.

8. The method according to claim 1, wherein the rAAV particles consist of rAAV4 particles containing DNA comprising an expression cassette encoding human RPE65.

9. The method according to claim 1, wherein said purified rAAV particles are suitable for use in gene therapy and further comprise a heterologous nucleic acid encoding a gene product.

10. The method according to claim 9, wherein said heterologous nucleic acid encoding gene product encodes a hormone, a growth receptor, a ligand, a protein, a siRNA, an antisense molecule, a miRNA, or a ribozyme.

11. The method according to claim 1, wherein the rAAV particles belong to the AAV serotype AAVrh10.

12. The method according to claim 1, wherein the rAAV particles belong to the AAV serotype AAV2.

* * * * *